(12) United States Patent
Skrzypczynski et al.

(10) Patent No.: US 7,297,780 B2
(45) Date of Patent: Nov. 20, 2007

(54) REACTIVE FUNCTIONAL GROUPS FOR PREPARATION OF MODIFIED NUCLEIC ACID

(75) Inventors: Zbigniev Skrzypczynski, Verona, WI (US); Sarah R. Wayland, Madison, WI (US)

(73) Assignee: Third Wave Technologies, Inc.

( * ) Notice: Subject to any disclaimer, the term of this patent is extended or adjusted under 35 U.S.C. 154(b) by 482 days.

(21) Appl. No.: 10/752,200

(22) Filed: Jan. 6, 2004

(65) Prior Publication Data

US 2004/0219576 A1   Nov. 4, 2004

Related U.S. Application Data

(60) Provisional application No. 60/438,252, filed on Jan. 6, 2003.

(51) Int. Cl.
    C07H 21/04    (2006.01)
(52) U.S. Cl. ..................................... 536/23.1
(58) Field of Classification Search ............... None
    See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,403,711 A | 4/1995 | Walder et al. |
| 5,409,818 A | 4/1995 | Davey et al. |
| 5,432,272 A | 7/1995 | Benner |
| 5,474,796 A | 12/1995 | Brennan |
| 5,538,848 A | 7/1996 | Livak et al. |
| 5,624,802 A | 4/1997 | Urdea et al. |
| 5,660,988 A | 8/1997 | Duck et al. |
| 5,710,264 A | 1/1998 | Urdea et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,858,659 A | 1/1999 | Sapolsky et al. |
| 5,882,867 A | 3/1999 | Ullman et al. |
| 5,912,340 A | 6/1999 | Kutyavin et al. |
| 5,914,230 A | 6/1999 | Liu et al. |
| 5,919,626 A | 7/1999 | Shi et al. |
| 5,925,525 A | 7/1999 | Fodor et al. |
| 5,952,174 A | 9/1999 | Nikiforov et al. |
| 5,958,692 A | 9/1999 | Cotton et al. |
| 5,985,551 A | 11/1999 | Brennan |
| 5,985,557 A | 11/1999 | Prudent et al. |
| 5,994,069 A | 11/1999 | Hall et al. |
| 6,001,311 A | 12/1999 | Brennan |
| 6,001,567 A | 12/1999 | Brow et al. |
| 6,001,983 A | 12/1999 | Benner |
| 6,013,170 A | 1/2000 | Meade |
| 6,017,696 A | 1/2000 | Heller |
| 6,037,120 A | 3/2000 | Benner |
| 6,045,996 A | 4/2000 | Cronin et al. |
| 6,051,380 A | 4/2000 | Sosnowski et al. |
| 6,063,573 A | 5/2000 | Kayyem |
| 6,068,818 A | 5/2000 | Ackley et al. |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,127,121 A | 10/2000 | Meyer, Jr. et al. |
| 6,140,496 A | 10/2000 | Benner |
| 6,143,877 A | 11/2000 | Meyer, Jr. et al. |
| 6,150,097 A | 11/2000 | Tyagi et al. |
| 6,183,960 B1 | 2/2001 | Lizardi |
| 6,210,884 B1 | 4/2001 | Lizardi et al. |
| 6,221,583 B1 | 4/2001 | Kayyem et al. |
| 6,248,229 B1 | 6/2001 | Meade |
| 6,348,314 B1 | 2/2002 | Prudent et al. |
| 6,458,535 B1 | 10/2002 | Hall et al. |

FOREIGN PATENT DOCUMENTS

| | | |
|---|---|---|
| WO | WO 97/27214 | 7/1997 |
| WO | WO 98/42873 | 10/1998 |
| WO | WO 99/67641 | 12/1999 |
| WO | WO 00/39587 | 7/2000 |

OTHER PUBLICATIONS

Jones et al., Conjugates of Double-Stranded Oligonucleotides with Poly(ethylene glycol) and Keyhole Limpet Hemocynanin: A Model for Treating Systemic Lupus Erythematosus, Bioconjugafe Chem. 1994, 5, 390-399.*
Letsinger and Lunsdorf, "Synthesis of thymidine oligonucleotides by phosphite triester intermediates," (1976) J. Am. Chem. Soc. 98:3655-3661.
Beaucage and Iyer, "Advances in the Synthesis of Oligonucleotides by the Phosphoramidite Approach," (1992) Tetrahedron, 48: 2223-2311.
Matray et al., "Synthesis of oligonucleotides containing 3'-alkylcarboxylic acids using a palladium labile oligonucleotide solid phase synthesis support," (1997) Bioconjugate Chem 8:99-102.
Lyttle et al., "Versatile linker chemistry for synthesis of 3'-modified DNA," (1997) Bioconjugate Chem. 8:193-198.
Agrawal and Iyer, Modified oligonucleotides as therapeutic and diagnostic agents, (1995) Curr. Opin. Biotechnol. 6:12-19.
Zhao et al., "Immobilization of oligodeoxyribonucleotides with multiple anchors to microchips," (2001) Nucleic Acids Res. 29:955-959.

(Continued)

Primary Examiner—Teresa E. Strzelecka
Assistant Examiner—Mark Staples
(74) Attorney, Agent, or Firm—Casimir Jones, S.C.

(57) ABSTRACT

The present invention relates to compositions and methods for the preparation of modified nucleic acids. In particular, the present invention provides novel reagents and chemistries for the generation of linkers and modified phosphoramidites.

3 Claims, 14 Drawing Sheets

OTHER PUBLICATIONS

Barany, "Genetic Disease Detection and DNA Amplification Using Cloned Thermostable Ligase," Proc. Natl. Acad. Sci USA 88, 189-93 (1991).
Habus et al., "A Mild and Efficient Solid-Support Synthesis of Novel Oligonucleotide Conjugates," (1998) Bioconjugate Chem. 9: 283-291.
Stetsenko et al., "Genetic Disease Detection and DNA Amplification Using Cloned Thermostable Ligase ," (2001) Bioconjugate Chem. 12:576-586.
Marshall, "Tumor suppressor genes," Cell, 64: 313-326 (1991).
Hausch and Jäschke, "Multifuncational dinucleotide analogs for the generation of complex RNA conjugates," (2001) Tetrahedron Lett. 57, 1261-1268.
Walton et al., "Evaluation of new linkers and synthetic methods for internal modified oligonucleotides," (2002) Bioconjug Chem 13, 1155-1158.
Sojka et al., "A novel phosphoramidite method for automated synthesis of oligonucleotides on glass supports for biosensor development," (2000) Appl Biochem Biotechnol 89, 85-103.
Vogel et al., "A substituted triaza crown ether as a binding site in DNA conjugates," (2003) Chem Commun 21(8):1006-1007.
Wu, X., and Pitsch, S., "Synthesis and pairing properties of oligoribonucleotide analogues containing a metal-binding site attached to beta-D-allofuranosyl cytosine," (1998) Nucleic Acids Res 26, 4315-4323.
Niemeyer, "The developments of semisynthetic DNA-protein conjugates," 20:395-401(2002).
Guzaev et al., "A New Approach for Chemical Phosphorylation of Oligonucleotides at the 5'-Terminus," Tetrahedron 51:9375-9384 (1995).
US 5,962,233 (withdrawn).
Caruthers et al., (1987) Methods Enzymol. 154:287-313.
Guzayev et al., (1995) Tetrahedron 51, 9375-9384.
Matysiak et al., (1997) Nucleosides & Nucleotides 16:855-861.
Nielsen, et al. Anticancer Drug Des. 8:53 63 [1993].
Trevisiol et al., (2000) Nucleosides, Nucleotides & Nucleic Acids 19:1427-1439.
Krotz et al., (2001) Bioorg. Med.Chem. Lett. 11:1863-1867.
Defrancq and Lhomme, (2001) Biorg. Med. Chem. Lett. 11:931-3.
Asseline and Thuong (1997) New J. Chem. 21: 5-17.
Zatsepin et al., (2002) Bioconjugate Chem. 13(4):822-830.
Forget et al., (2001) Tetrahedron Lett. 42, 7829-7832.
Podyminogin et al., (2001) Nucleic Acids Res. 29:5090-5098.
Lindroos et al., (2001) Nucleic Acids Res. 29:e69.
Dombi et al., (2002) Synthesis 6: 816-824.
Tilquin et al., (2001) Bioconjugate Chem. 12:451-457.
Karino et al., (2001) Nucleic Acids Res. 29: 2456-2463.
Ruth, (1994) Methods in Molecular Biology 26, 167-185.
Salo et al., (1999) Bioconjugate Chem. 10:815-823.
Forget et al., (2001) Chem. Eur. J. 7: 3976-3984.
Weinberg, Science, 254: 1138-1146 (1991).
Lyamichev et al., Nat. Biotech., 17:292 (1999).
Hall et al., PNAS, USA, 97:8272 (2000).
Hovinen et al., (1993) Tetrahedron Lett. 34:5163-5166.
Montserat et al., (1993) Nucleotides, Nucleosides 12:967-971.
Allawi, H.T. & SantaLucia, J., Jr. Thermodynamics and NMR of internal G. T mismatches in DNA. Biochemistry 36, 10581-94 (1997).
Pon and Yu (1997) Nucleic Acids Res. 25: 3629-363.
Greenberg and Kahl (2001) J.Org.Chem. 66:7151-7154.
Czaplinski and Sheppard, (2001) J. Am. Chem. Soc. 123:8618-8619.
Watterson et al., (2000) Langmuir 16, 4984-4992.
Steel et al., (2000) Biophys. J. 79, 975-81.
Shchepinov et al., (1997) Nucleic Acids Res. 25, 1155-1161.
Jäschke et al., (1993) Tetrahedron Lett. 34, 301-304.
Greenwald et al., (2000) Crit. Rev. Ther. Drug Carrier Syst. 17, 101-61.
Bonora et al., (1997) Bioconjugate Chem. 8, 793-797.
Jäschke et al., (1994) Nucleic Acids Res. 22, 4810-4817.
Jäschke et al., (1996) Nucleosides, Nucleotides 15, 1519-1529.
Afanassiev et al., (2000) Nucleic Acid Res. 28, E66-e66.
Hermanson, G.T. (1996) Bioconjugate techniques. Academic Press, pp. 185-186.
Urata et al., (1993) Tetrahedron Lett. 34,4015-4018.
Horn et al., (1997) Nucleic Acids Res. 25, 4842-4849.
McBride et al., (1988) Biotechniques 6, 362-7.
US 5,962,233, 10/1999, Livak et al. (withdrawn)

* cited by examiner

7 ; n= 2

(5')HO-dT$_n$-O-P(O$_2$)-O-(CH$_2$)$_6$-C(=O)—H

8; n = 10

1. H$_2$N-R / 25mM sodium borate buffer, pH9.5
   a) H$_2$N-R = 4,7,10-trioxa-1,13-tridecaneamine
   b) H$_2$N-R = 1-pyrene methylamine
2. NaBH$_3$CN (5')HO-dT$_n$-O-P(O$_2$)-O-(CH$_2$)$_6$-CH$_2$-NH-R 9a, n = 10 ; R = 4,7,10-trioxa-1,13-tridecaneamine
9b, n = 10 ; R = 1-methylpyrene 3'HO—dT$_{10}$—O-P(O$_2$)-O-R-NH-C(O)-(CH$_2$)$_7$-C(O)H

13a; R = C$_6$H$_{12}$

1. H$_2$N-(CH$_2$)$_3$[(CH$_2$)$_4$O]$_n$-(CH$_2$)$_3$-NH$_2$ ; (Av. M.W. 1100)

14

2. NaBH$_3$CN / Phosphate Buffer pH 9

(3')OH— dT$_{10}$-O-P(O$_2$)-O-C$_6$H$_{12}$-NH-C(O)-(CH$_2$)$_7$-CH(OH)-CH(OH)-(CH$_2$)$_6$-O-DMT

16

(3')OH— dT$_{10}$-O-P(O$_2$)-O-C$_6$H$_{12}$-NH-(O)C-(CH$_2$)$_7$-CH(OH)-CH(OH)-(CH$_2$)$_6$-O-P(O$_2$)-O-R-OH

17; R = C$_{12}$H$_{25}$ (3')OH— dT$_5$—O-P(O$_2$)-O-C$_6$H$_{12}$-NH-(O)C-(CH$_2$)$_7$-CH(OH)-CH(OH)-(CH$_2$)$_6$-O-P(O$_2$)-O-dT$_{10}$-O-P(O$_2$)-FAM

18 ; FAM = Fluorescein

Steps:
1. applying to the C18-OPC column
2. elution of truncated fragments
3. sodium periodate oxidation
4. elution of sodium periodate
5. elution of the oxidized product 13a (3')OH— dT$_{10}$–O-P(O$_2$)-O-C$_6$H$_{12}$-NH-(O)C-(CH$_2$)$_7$-C(O)H 13a

Figure 13

REACTIVE FUNCTIONAL GROUPS FOR PREPARATION OF MODIFIED NUCLEIC ACID

The present Application claims priority to U.S. Provisional Application Ser. No. 60/438,252, filed Jan. 6, 2003, which is incorporated herein by reference.

FIELD OF THE INVENTION

The present invention relates to compositions and methods for the preparation of modified nucleic acids. In particular, the present invention provides novel reagents and chemistries for the generation of linkers and modified phosphoramidates.

BACKGROUND

Oligonucleotides are important materials for research, diagnostic, therapeutic and other purposes. An ever-growing demand for improved oligonucleotides, oligonucleotide analogs and for methods for their preparation and use has arisen.

Modified oligonucleotides are of particular value in molecular biological applications. For example, modified oligonucleotides (e.g., oligonucleotides comprising moieties that are detectable, or that confer altered hybridization properties), find use in diverse areas, e.g., as aids in molecular biology, as pharmaceutical compounds, or as diagnostic agents. Modified oligonucleotides that can block RNA translation are useful as inhibitors of gene expression (e.g., as antisense oligonucleotides, small interfering RNAs (siRNAs), microRNAs (miRNAs), ribozymes, sense oligonucleotides and triplex-forming oligonucleotides).

The discovery of the phosphoramidite method for automated synthesis of natural and modified DNA molecules (Letsinger and Lunsdorf (1976) J. Am. Chem. Soc. 98:3655-3661; Caruthers et al., (1987) Methods Enzymol. 154:287-313; Beaucage and Iyer (1992) Tetrahedron, 48: 2223-2311; Protocols for Oligonucleotides and Analogs. Methods in Molecular Biology, Vol 20, Edited by Sudhir Agraval, Humana Press 1993) has stimulated the development of numerous reagents and methods to introduce specific modifications or functional groups at selected positions within synthesized oligonucleotides (Guzayev et al., (1995) Tetrahedron 51, 9375-9384; Matray et al., (1997) Bioconjugate Chem. 8:99-102; Lyttle et al., (1997) Bioconjugate Chem. 8:193-198).

In some applications it is desirable to label or tag oligonucleotides, (e.g., attach a dye or another functional moiety). Some phosphoramidite reagents comprising tags or labels are commercially available. However, escalating interest in the use of modified synthetic oligonucleotides in the disciplines of biology, medicine, and biotechnology (Agraval and Iyer (1999) Curr. Opin. Biotechnol. 6:12-19; Delivery Strategies for Antisense Oligonucleotide Therapeutics. Ed. Saghir Akhtar, CRC Press, 1995; Matysiak et al., (1997) Nucleosides & Nucleotides 16:855-861; Zhao et al., (2001) Nucleic Acids Res. 29:955-959) has intensified the need for less expensive and more broadly applicable labeling reagents. Some efforts have been focused on the development of strategies for the preparation of oligonucleotides that can be conjugated with other molecules and biological moieties, or attached to solid surfaces post-synthetically (i.e., after synthesis of the oligonucleotide). Some strategies for post-synthetic labeling have made use of synthesis reagents that produce oligonucleotides comprising one or more reactive amine groups or reactive thiol groups. While these reagents are useful in many applications, there remains a need for efficient and cost effective compositions and methods for modifying and conjugating oligonucleotides.

SUMMARY OF THE INVENTION

The present invention relates to compositions and methods for the preparation of modified nucleic acids. In particular, the present invention provides novel reagents and chemistries for the generation of linkers and modified phosphoramidates. In some preferred embodiments, the compositions of the present invention find use in the synthesis of oligonucleotides comprising one or more reactive functional groups.

Accordingly, in some embodiments, the present invention provides a composition comprising:

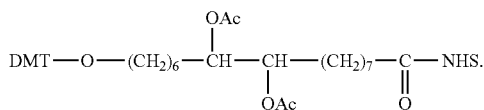

In other embodiments, the present invention provides a modified synthesis support, (e.g., CPG® (controlled pore glass)) comprising the composition. In yet other embodiments, the present invention provides a modified phosphoramidite comprising the composition.

The present invention further provides a composition comprising a nucleic acid comprising the structure:

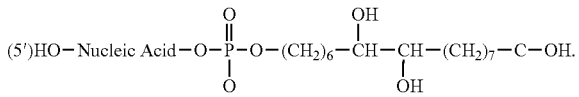

The present invention additionally provides a composition comprising a nucleic acid comprising the structure:

(5')HO-Nucleic Acid —O—P(O$_2$)—O—(CH$_2$)$_6$—CH$_2$—NH—R.

In some embodiments, R is a label. In some embodiments, the label is selected from the group including, but not limited to, fluorescent labels, chemiluminescent labels, and enzymatically reactive labels. In other embodiments, R is a biological molecule.

The present invention also provides a composition comprising a phosphoramidite comprising the structure:

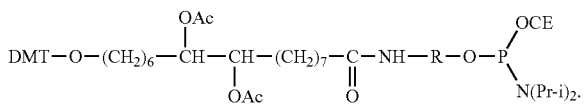

In some embodiments, R is selected from the group including, but not limited to, C$_6$H$_{12}$ and polyethylene glycol 3400. In some embodiments, R is a label. In some embodiments, the label is selected from the group including, but not limited to, fluorescent labels, chemiluminescent labels, and enzymatically reactive labels. In some embodiments, R is a biological molecule.

In yet other embodiments, the present invention provides a composition comprising the structure:

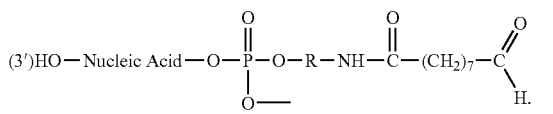

In some embodiments, R is a label. In some embodiments, the label is selected from the group including, but not limited to, fluorescent labels, chemiluminescent labels, and enzymatically reactive labels. In some embodiments, R is a biological molecule.

In still further embodiments, the present invention provides a composition comprising a nucleic acid comprising a structure selected from the group consisting of:

(3')OH-nucleic acid-O—P($O_2$)—O—$C_6H_{12}$—NH—C(O)—$(CH_2)_7$—CH(OH)—CH(OH)—$(CH_2)_6$—O-DMT (3')OH-nucleic acid-O—P($O_2$)—O—$C_6H_{12}$—NH—(O)C—$(CH_2)_7$—CH(OH)—CH(OH)—$(CH_2)_6$—O—P($O_2$)—O—R—OH (3')OH-nucleic acid-O—P($O_2$)—O—$C_6H_{12}$—NH—(O)C—$(CH_2)_7$—C(O)H and (3')OH-nucleic acid-O—P($O_2$)—O—$C_6H_{12}$—NH—(O)C—$(CH_2)_7$—CH(OH)—CH(OH)—$(CH_2)_6$—O—P($O_2$)—O-nucleic acid-O—P($O_2$)-FAM In some embodiments, R is $C_{12}H_{25}$.

In some embodiments, the present invention provides a kit comprising a nucleic acid labeling reagent selected from the group consisting of:

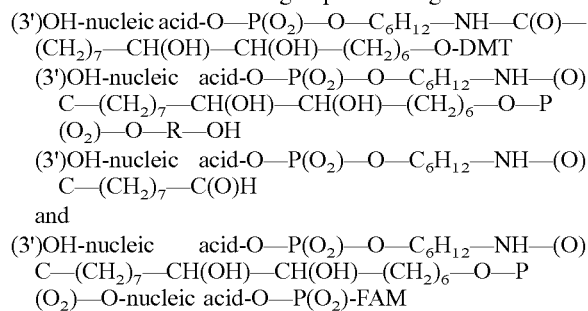

(3')OH-nucleic acid-O—P($O_2$)—O—$C_6H_{12}$—NH—C(O)—$(CH_2)_7$—CH(OH)—CH(OH)—$(CH_2)_6$—O-DMT (3')OH-nucleic acid-O—P($O_2$)—O—$C_6H_{12}$—NH—(O)C—$(CH_2)_7$—CH(OH)—CH(OH)—$(CH_2)_6$—O—P($O_2$)—O—$R_3$—OH (3')OH-nucleic acid-O—P($O_2$)—O—$C_6H_{12}$—NH—(O)C—$(CH_2)_7$—C(O)H and (3')OH-nucleic acid-O—P($O_2$)—O—$C_6H_{12}$—NH—(O)C—(CH2)$_7$—CH(OH)—CH(OH)—$(CH_2)_6$—O—P($O_2$)—O-nucleic acid-O—P($O_2$)-FAM In some embodiments, $R_1$ is selected from the group including, but not limited to, $C_6H_{12}$ and polyethylene glycol 3400. In some embodiments, $R_1$, $R_2$ and $R_3$ are labels. In some embodiments, the labels are selected from the group including, but not limited to, fluorescent labels, chemiluminescent labels, and enzymatically reactive labels. In other embodiments, $R_1$, $R_2$ and $R_3$ are biological molecules. In some embodiments, $R_3$ is $C_{12}H_{25}$.

The present invention further provides a method of labeling nucleic acids, comprising providing a nucleic acid labeling reagent selected from the group consisting of:

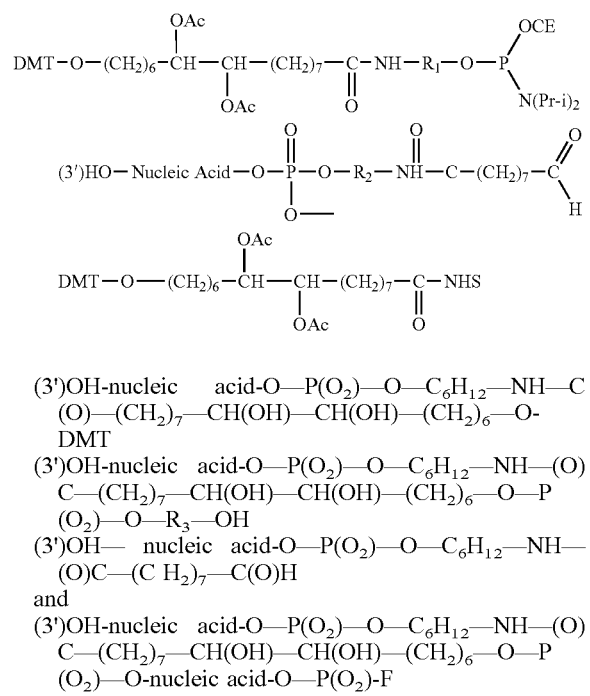

(3')OH-nucleic acid-O—P($O_2$)—O—$C_6H_{12}$—NH—C(O)—$(CH_2)_7$—CH(OH)—CH(OH)—$(CH_2)_6$—O-DMT (3')OH-nucleic acid-O—P($O_2$)—O—$C_6H_{12}$—NH—(O)C—$(CH_2)_7$—CH(OH)—CH(OH)—$(CH_2)_6$—O—P($O_2$)—O—$R_3$—OH (3')OH— nucleic acid-O—P($O_2$)—O—$C_6H_{12}$—NH—(O)C—(C $H_2)_7$—C(O)H and (3')OH-nucleic acid-O—P($O_2$)—O—$C_6H_{12}$—NH—(O)C—$(CH_2)_7$—CH(OH)—CH(OH)—$(CH_2)_6$—O—P($O_2$)—O-nucleic acid-O—P($O_2$)-F and contacting the nucleic acid labeling reagent with a nucleic acid under conditions such that the nucleic acid labeling reagent is covalently linked to the nucleic acid. In some embodiments, the nucleic acid labeling reagent is attached to a CPG. In other embodiments, the nucleic acid labeling reagent is attached to a second nucleic acid. In still further embodiments, the nucleic acid labeling reagent is attached to a solid support. In some embodiments, the solid support comprises an array of the nucleic acid labeling reagents. In some embodiments, the nucleic acid is an oligonucleotide. In some embodiments, $R_1$ is selected from the group including, but not limited to, $C_6H_{12}$ and polyethylene glycol 3400. In some embodiments, $R_1$, $R_2$ and $R_3$ are labels. In some embodiments, the labels are selected from the group including, but not limited to, fluorescent labels, chemiluminescent labels, and enzymatically reactive labels. In other embodiments, $R_1$, $R_2$ and $R_3$ are biological molecules. In some embodiments, $R_3$ is $C_{12}H_{25}$.

DESCRIPTION OF THE FIGURES

FIG. 2 shows steps in the synthesis of the NHS ester of the selectively protected aleuritic acid 3a.

FIG. 11 shows a schematic of the reductive amination coupling of the 5'-aldehyde modified probe 13a to the bis-(3-aminopropyl)terminated polytetrahydroduran 14.

FIG. 12 shows the structures of synthesized compounds 16, 17 and 18.

FIG. 13 shows a schematic of the preparation of the 5'-aldehyde modified probe 13a via sodium periodate oxidation of the 5'-aleuritic acid modified probe 17 absorbed on the C18-OPC cartridge.

DEFINITIONS

Figure 1:
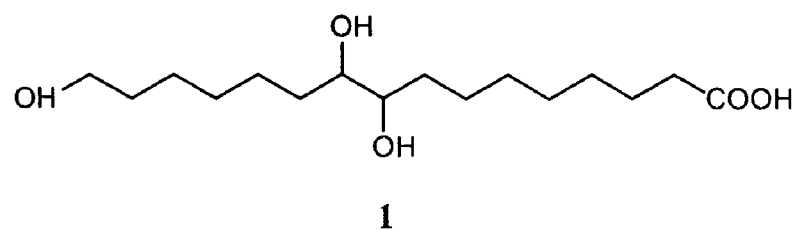
FIG. 1 shows the structure of aleuritic acid 1.

As used herein, the terms "X, Y, $R_1$ and $R_2$" refer to any atom or molecule attached to another molecule (e.g., a reagent of the present invention), unless specifically identified otherwise.

As used herein, the term "reactive functional group" refers to any atom or group of atoms that can be reacted to form a chemical bond with an atom or group of atoms that are not part of the reactive functional group (e.g., to form a covalent bond with a nucleic acid or surface).

As used herein, the term "nucleic acid labeling reagent" refers to any reagent that is used to introduce a modification (e.g., a reactive functional group or a label) into a nucleic acid (e.g., an oligonucleotide). In some embodiments, nucleic acid labeling reagents comprise the aleuritic acid derivatives of the present invention. In some embodiments nucleic acid labeling reagents include, but are not limited to, modified synthesis solid supports, modified phosphoramidites, and modified linkers. The nucleic acid labeling reagents of the present invention may be used to introduce any desired modification (e.g., including, but not limited to, labels as defined below, reactive functional groups, supports and biological molecules) into or onto a nucleic acid. In some embodiments of the present invention a nucleic acid labeling reagent is covalently linked to a nucleic acid. In some embodiments, a nucleic acid labeling reagent may undergo chemical reaction comprising loss of an atom or side group (e.g., H, or OH groups), or other minor alteration in composition as a result of the linkage reaction. The use of the term "nucleic acid labeling reagent" is intended to include the forms of the reagent both before and after any such changes caused by the covalent linkage to a nucleic acid.

The term "label" as used herein refers to any atom or molecule that can be used to provide a detectable effect, and that can be attached to a nucleic acid or protein. Labels include but are not limited to dyes such as fluorescein, CASCADE BLUE, hexachloro-fluorescein, tetrachloro-fluorescein, TAMRA, ROX, VIC, JOE, Cy3, Cy3.5, Cy5, Cy5.5, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaz-a-S-indacene-propionic acid, 6-carboxy-X-rhodamine, N,N,N',N'-tetramethyl-6-carboxyrhodamine, TEXAS RED, eosin, 4,4-difluoro-5,7-diphenyl-4-bora-3a,4a-diaza-s-indacene-3-propionic acid, 4,4-difluoro-5,p-ethoxyphenyl-4-bora-3a,4a-diaza-s-indacene 3-propionic acid and 4,4-difluoro-5-styryl-4-bora-3a,4a-diaza-S-indacene-propionic acid, BOTHEL BLUE, REDMOND RED, YAKIMA YELLOW; radiolabels such as $^{32}p$; binding moieties such as biotin and minor groove binders (MGBs) such as distamycin and CC-1065 (Epoch Biosciences, Redmond Wash.); haptens such as digoxgenin; luminogenic, phosphorescent or fluorogenic moieties; and fluorescent dyes alone or in combination with moieties that can suppress or shift emission spectra by fluorescence resonance energy transfer (FRET). Labels comprise moieties that quench fluorescence or other energy emissions, "quenchers"), including but not limited to dabcyl, QSY7 (Molecular Probes, Eugene, Oreg.), and ECLIPSE quenchers (Synthetic Genetics, San Diego, Calif.). Labels may provide signals detectable by any means, including but not limited to, fluorescence, radioactivity, colorimetry, gravimetry, X-ray diffraction or absorption, magnetism, effects of mass (e.g., rotation, time-of-flight, etc), enzymatic activity, and the like. A label may be detected in any fashion, including but not limited to, by use of the unaided senses (e.g., by smell, sound, visual effect, etc.), by an instrument (e.g. a camera, fluorimeter, charge-coupled device, scintillation counter, polarimeter, spectrometer, etc.) or a reactive medium (X-ray or camera film, pH indicator, etc.), that can convey to a user or to another component of a system (e.g., a computer or controller) the presence of a signal or effect. Such detection may comprise detection of ultraviolet, visible or infrared light, including fluorescence or chemiluminescence; a radiation; a spectroscopic effect such as nuclear magnetic resonance, mass (e.g., by spectrometry) or surface enhanced Raman effects or plasmon resonance. A label may be a charged moiety (positive or negative charge) or alternatively, may be charge neutral. Labels can include or consist of a nucleic acid or protein sequence, so long as the sequence is detectable.

As used herein, the term "nucleic acid molecule" refers to any nucleic acid-containing molecule, including but not limited to, DNA (single and double-stranded), RNA (single and double-stranded), and peptide nucleic acid (PNA). The term encompasses sequences that include any of the known base analogs of DNA and RNA.

As used herein, the term "base analog" includes any of the known base analogs of DNA and RNA bases, including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. The term also includes modified or non-naturally occurring bases such as 7-deaza purines (e.g., 7-deaza-adenine and 7-deaza-guanine); bases modified, for example, to provide altered interactions such as non-standard basepairing, including, but not limited to: IsoC, Iso G, and other modified bases and nucleotides described in U.S. Pat. Nos. 5,432,272; 6,001,983; 6,037,120; 6,140,496; 5,912,340; 6,127,121 and 6,143,877, each of which is incorporated herein by reference in their entireties; heterocyclic base analogs based no the purine or pyrimidine ring systems, and other heterocyclic bases. Nucleotide analogs include base analogs and comprise modified forms of deoxyribonucleotides as well as ribonucleotides.

The term "peptide nucleic acid" ("PNA") as used herein refers to a molecule comprising bases or base analogs such as would be found in natural nucleic acid, but attached to a peptide backbone rather than the sugar-phosphate backbone typical of nucleic acids. The attachment of the bases to the peptide is such as to allow the bases to base pair with complementary bases of nucleic acid in a manner similar to that of an oligonucleotide. These small molecules, also designated anti gene agents, stop transcript elongation by binding to their complementary strand of nucleic acid (Nielsen, et al. Anticancer Drug Des. 8:53 63 [1993]).

The term "adduct" is used herein in its broadest sense to indicate any compound or element that can be added to an oligonucleotide. An adduct may be charged (positively or negatively) or may be charge-neutral. An adduct may be added to the oligonucleotide via covalent or non-covalent linkages. Examples of adducts include, but are not limited to, indodicarbocyanine dye amidites, amino-substituted nucleotides, ethidium bromide, ethidium homodimer, (1,3-propanediamino)propidium, (diethylenetriamino)propidium, thiazole orange, (N—N'-tetramethyl-1,3-propanediamino)propyl thiazole orange, (N—N'-tetramethyl-1,2-ethanediamino)propyl thiazole orange, thiazole orange-thiazole orange homodimer (TOTO), thiazole orange-thiazole blue heterodimer (TOTAB), thiazole orange-ethidium heterodimer 1 (TOED1), thiazole orange-ethidium heterodimer 2 (TOED2) and fluorescein-ethidium heterodimer (FED), psoralens, biotin, streptavidin, avidin, etc.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the term "oligonucleotide," refers to a short polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "synthetic oligonucleotide" refers to an oligonucleotide that is chemically synthesized, e.g., from precursors such as phosphoramidites. Synthetic oligonucleotides may be produced using a number of synthesis chemistries, including but not limited to phosphoramidite chemistry and phosphite-triester chemistry.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand. Nucleotide analogs used to form non-standard base pairs, whether with another nucleotide analog (e.g., an IsoC/IsoG base pair), or with a naturally occurring nucleotide (e.g., as described in U.S. Pat. No. 5,912,340, herein incorporated by reference in its entirety) are also considered to be complementary to a base pairing partner within the meaning this definition. Further, when nucleotides are known to form pairs with multiple different bases, e.g., IsoG nucleotide ability to pair with IsoC and with T nucleotides, each of the bases with which it can form a hydrogen-bonded base-pair falls within the meaning of "complementary," as used herein. "Universal" bases, i.e., those that can form base pairs with several other bases, such as the "wobble" base inosine, are considered complementary to those bases with which pairs can be formed.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See e.g., Anderson and Young, Quantitative Filter Hybridization, in Nucleic Acid Hybridization [1985]). Other references (e.g., Allawi, H.T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of $T_m$.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc).

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as DNA polymerase and at a suitable temperature and pH).

As used herein, the term "probe" refers to an oligonucleotide, whether occurring naturally as in a purified restriction digest or produced synthetically, recombinantly or by PCR amplification, that is capable of hybridizing to another nucleic acid of interest. A probe may be single-stranded or double-stranded. In some embodiments of the present invention a probe comprises a label.

As used herein, the term "target" refers to a nucleic acid, or a region of nucleic acid that is sought to be sorted out from other nucleic acid sequences. In some embodiments, the target nucleic acid is a nucleic acid or a region of a nucleic acid containing a mutation or polymorphism of interest.

As used herein, the term "polymerase chain reaction" ("PCR") refers to the method of K. B. Mullis U.S. Pat. Nos. 4,683,1954,683,202, and 4,965,188, hereby incorporated by reference, which describe a method for increasing the concentration of a segment of a target sequence in a mixture of genomic DNA without cloning or purification. This process for amplifying the target sequence comprises introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications. As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the terms "solid support" or "support" refer to any material that provides a solid or semi-solid structure with which another material can be attached. Such materials include smooth supports (e.g., metal, glass, plastic, silicon, and ceramic surfaces) as well as textured and porous materials. Such materials also include, but are not limited to, gels, rubbers, polymers, and other non-rigid materials. Solid supports need not be flat. Supports include any type of shape including spherical shapes (e.g., beads). Materials attached to solid support may be attached to any portion of the solid support (e.g., may be attached to an interior portion of a porous solid support material).

As used herein, the term "bead" refers to a small solid support that is capable of moving about in a solution (i.e., it has dimensions smaller than those of the enclosure in which it resides). In some embodiments, beads are completely or partially spherical or cylindrical. However, beads are not limited to any particular three-dimensional shape.

As used herein, the term "microarray" refers to a solid support with a plurality of molecules (e.g., oligonucleotides) bound to its surface. Microarrays, for example, are described generally in Schena, "Microarray Biochip Technology," Eaton Publishing, Natick, Mass., 2000. Additionally, the term "patterned microarrays" refers to microarray substrates with a plurality of molecules non-randomly bound to its surface.

DETAILED DESCRIPTION OF THE INVENTION

The present invention provides an efficient and versatile preparative method for the preparation of nucleic acid probes modified at their 3' or 5'-ends with an aldehyde group. In some embodiments, the synthetic strategy of the present invention provides a new family of phosphoramidites and solid supports that are compatible with the automated synthesis of modified oligonucleotides. In some embodiments, these novel reagents are prepared from a common intermediate obtained from commercially available aleuritic acid. In further embodiments, the novel phosphoramidite reagents of the present invention are used as cleavable linkers. In yet other embodiments, the novel reagents of the present invention are used to attach nucleic acids to a solid support.

I. Reagents

In some embodiments, the present invention provides reagents for use in the production of modified nucleic acids. Experiments conducted during the course of development of the present invention resulted in the synthesis of novel reagents useful in the labeling of nucleic acids in a wide variety of methods.

In some embodiments, commercially available aleuritic acid (DL-erythro-9,10,16-Trihydroxypalmitic acid) 1 is used as a starting material for the preparation of the novel labeling reagents of the present invention. The structural features of aleuritic acid 1 offer ample opportunities for the preparation of new types of phosphoramidite reagents that can introduce both a carboxyl group and a masked aldehyde group into a synthesized DNA probe, or can be used for the preparation of a new family of cleavable linkers. Carboxyl and aldehyde groups play particularly significant roles in the post-synthetic modification of oligonucleotide probes (Ermolinsky and Mikhailov (2000) Russian Journal of Bioorganic Chemistry 26:429-449; Trevisiol et al., (2000) Nucleosides, Nucleotides & Nucleic Acids 19:1427-1439; Krotz et al., (2001) Bioorg. Med. Chem. Lett. 11:1863-1867; Defrancq and Lhomme, (2001) Biorg. Med. Chem. Lett. 11:931-3), preparation of oligonucleotide conjugates (Forget et al., (2001) Chem. Eur. J. 7: 3976-3984; Asseline and Thuong (1997) New J. Chem. 21: 5-17; Zatsepin et al., (2002) Bioconjugate Chem. 13(4):822-830; Forget et al., (2001) Tetrahedron Lett. 42, 7829-7832) and immobilization of DNA probes onto amino-modified solid surfaces (Podyminogin et al., (2001) Nucleic Acids Res. 29:5090-5098; Lindroos et al., (2001) Nucleic Acids Res. 29:e69; Dombi et al., (2002) Synthesis 6: 816-824). Several recent papers, highlighting the use of DNA probes modified at their 3' or 5' terminus with different functional groups (Podyminogin et al., supra) demonstrate the superiority of the aldehyde group in post-synthetic conjugation and immobilization techniques compared to other functional groups.

The synthesis of new reagents allowing for the introduction of an aldehyde group into DNA probes has been reported recently (Tilquin et al., (2001) Bioconjugate Chem. 12:451-457; Karino et al., (2001) Nucleic Acids Res. 29: 2456-2463; Ruth, (1994) Methods in Molecular Biology 26, 167-185; Salo et al., (1999) Bioconjugate Chem. 10:815-823; Podyminogin et al., supra; Dombi et al., (2002) Synthesis 6:816-824). Experiments conducted during the course of development of the present invention (See Experimental Section) demonstrated that the aleuritic acid intermediates 3a can serve as intermediates in the synthesis of a new family of structurally diverse phosphoramidites 11, modified solid supports, and linkers that possess the capability of introducing a masked aldehyde group into a synthesized DNA probe. The masked aldehyde group can then be further modified for the inclusion of conjugates or linkers of interest. The aldehyde modified reagents of the present invention find use in the generation of a variety of modified nucleic acids.

II. Modified Nucleic Acids

The reagents of the present invention find use in the synthesis of aldehyde modified nucleic acids, for the preparation of new types of cleavable linkers, for the conjugation of biomolecules to nucleic acids and for the attachment of nucleic acids to solid supports. In some embodiments, the aldehyde labeled nucleic acids or linkers serve as starting materials in conjugation reactions with other organic moieties containing primary amino groups. The mild reaction conditions leading to the introduction of the aldehyde group in DNA probes or leading to the cleavage of the aleuritic acid linker facilitates the preparation of aldehyde-labeled materials, even in the presence of sensitive organic groups. The present invention further provides a simple method to prepare DNA probes modified at their 5'-end with an aldehyde group.

A. Modified Solid Supports

In recent years, chemical literature has reported numerous methods for synthesizing different phosphoramidite reagents used to introduce single or multiple functional groups at the 3' or 5' terminus of a synthesized DNA oligonucleotide (Guzayev et al., (1995) Tetrahedron 51, 9375-9384; Matray et al., (1997) Bioconjugate Chem. 8:99-102; Lyttle et al., (1997) Bioconjugate Chem. 8:193-198). In contrast, far fewer methods are reported for utilizing a specifically modified solid support to synthesize 3'-modified oligonucleotides (Habus et al., (1998) Bioconjugate Chem. 9: 283-291; Stetsenko et al., (2001) Bioconjugate Chem. 12:576-586; Hausch and Jaschke (2001) Tetrahedron 57:1261-1268), most likely due to the synthetic inconveniences associated with the preparation of such reagents. The methods of the present invention utilize the approach of synthesizing a solid support modified with an aleuritic acid moiety to introduce a carboxyl or masked aldehyde group into the 3'-end of a synthesized oligonucleotide, leaving the 5'-teminus available for other modifications.

In some embodiments, the present invention provides solid supports (e.g., CPG) modified with a reagent of the present invention. Such modified solid supports find use in the modification of synthesized nucleic acids at the 3' end. For example, in some embodiments, the aleuritic acid moiety is attached to the solid support. In some embodiments, following synthesis of the oligonucleotide and cleavage from the solid support, the aleuritic acid moiety is oxidized to form aldehyde functional groups. In some embodiments, aldehyde groups are then used in amination with amine compounds of interest (e.g., biomolecules or labels). Exemplary synthesis methods are described in the experimental section (See e.g., FIGS. 3, 4, 6 and 8).

B. Modified Phosphoramidites

Figure 9:
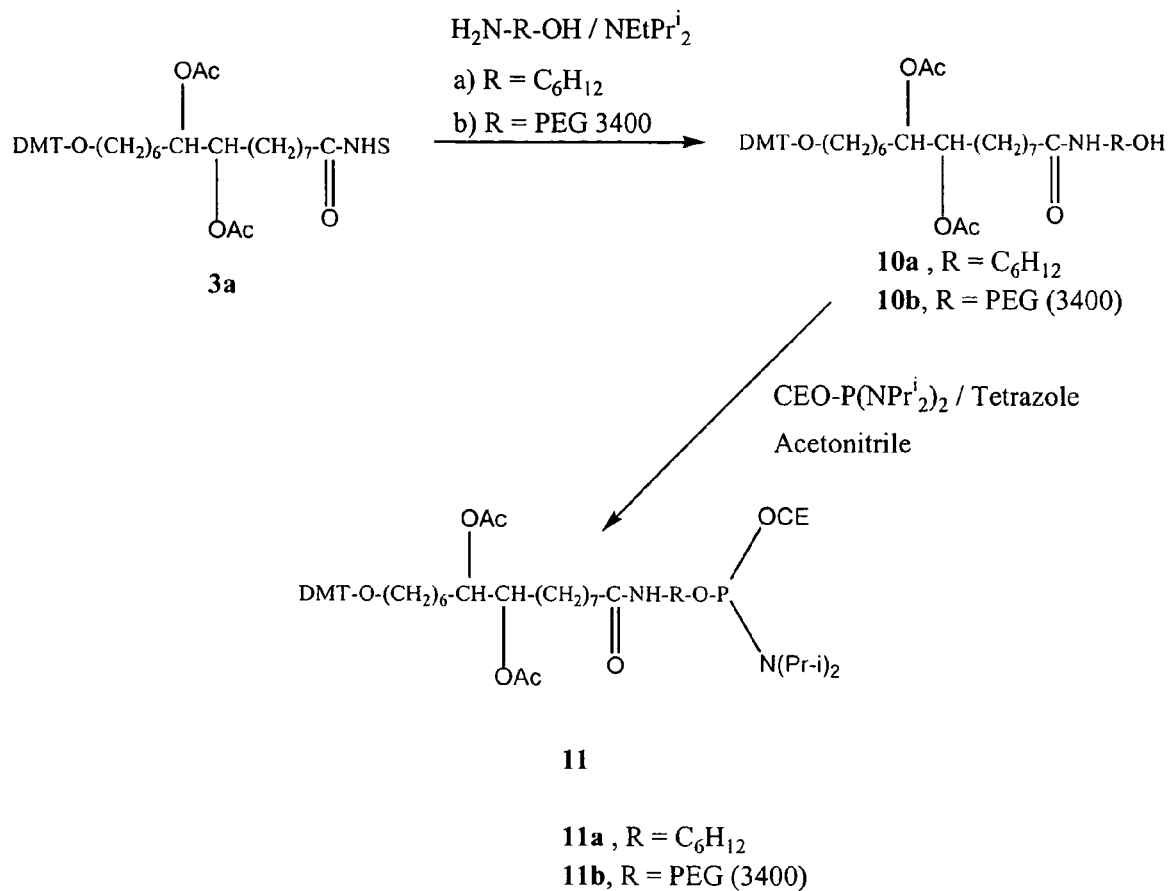
FIG. 9 shows a schematic of the synthesis of the phosphoramidites 11a and 11b.

In other embodiments, the aleuritic acid reagents of the present invention are utilized in the synthesis of modified phosphoramidites. FIG. 9 demonstrates an exemplary synthesis method for modifying an aleuritic acid phosphoramidite to include an R group of interest. In some embodiments, the modified phosphoramidites are then used in automated synthesis methods to generate modified oligonucleotides. In some embodiments, following synthesis, the aleuritic acids moieties of the modified phosphoramidites are oxidized to aldehydes. In some embodiments, the aldehyde labeled oligonucleotides serve as starting materials in conjugation reactions with other organic moieties containing primary amino groups.

C. Linkers

In still further embodiments, the reagents of the present invention are used in the synthesis of cleavable linkers. FIG. 12 shows the synthesis of exemplary cleavable linkers of the present invention. In some embodiments, cleavable linkers are used in the preparation of specific nucleic acids or conjugates. The mild reaction conditions leading to the cleavage of the aleuritic acid linker facilitates the preparation of aldehyde-labeled materials, even in the presence of sensitive organic groups.

In some embodiments, linkers are used to attach labels to nucleic acids (e.g., fluorescent or affinity labels). In other embodiments, linkers are used to attach any number of different biological molecules to oligonucleotides (e.g., proteins, lipids, carbohydrates, etc.) or to attach oligonucleotides to solid supports (See below description).

III. Applications

The modified nucleic acids of the present invention find use in any number of applications utilizing the labeling and detection of nucleic acids. The advent of large scale genomic projects and the increasing medical use of molecular diagnostics, has prompted the development of large volume throughput methods for screening recombinant DNA libraries representing entire genomes, the performance of large scale DNA sequencing projects, and executing replicative immunological assays, nucleic acid hybridization assays, or polymerase chain reaction assays. High throughput methods often rely on biomolecular arrays.

Many disease states are characterized by differences in the expression levels of various genes either through changes in the copy number of the gene's DNA or through changes in levels of transcription (e.g., through control of initiation, provision of RNA precursors, RNA processing, etc.) of particular genes. For example, losses and gains of genetic material play an important role in malignant transformation and progression. These gains and losses are thought to be "driven" by at least two kinds of genes. Oncogenes are positive regulators of tumorgenesis, while tumor suppressor genes are negative regulators of tumorgenesis (Marshall, Cell, 64: 313-326 (1991); Weinberg, Science, 254: 1138-1146 (1991)). Thus, changes in the expression (transcription) levels of particular genes (e.g. oncogenes or tumor suppressors), serve as signposts for the presence and progression of various cancers. Similarly, control of the cell cycle and cell development, as well as diseases, are characterized by the variations in the transcription levels of particular genes. Thus, for example, a viral infection is often characterized by the elevated expression of genes of the particular virus. Detection of elevated expression levels of characteristic viral genes provides an effective diagnostic of the disease state. In particular, viruses such as herpes simplex, enter quiescent states for periods of time only to erupt in brief periods of rapid replication. Detection of expression levels of characteristic viral genes allows detection of such active proliferative (and presumably infective) states. Exemplary, non limiting methods are described below.

A. Immobilization on a Solid Support

In some embodiments, the reagents of the present invention (e.g., the linkers described above) are used in the immobilization of nucleic acids on solid supports. Immobilized nucleic acids are used in many applications including, but not limited to, gene expression analysis, drug screening, nucleic acid sequencing, and mutation analysis. In some embodiments, arrays of nucleic acids are used in such applications.

B. Diagnostic Applications

In some embodiments, the labeled nucleic acids of the present invention find use in diagnostic applications (e.g., the detection of target nucleic acids). In some embodiments of the present invention, nucleic acid sequences labeled using the compositions and methods of the present invention are used in the detection of nucleic acid sequences. For example, in some embodiments, labeled nucleic acid sequences are hybridized to target nucleic acid sequences in a hybridization assay. In a hybridization assay, the presence or absence of a target nucleic acid sequence is determined based on the ability of the nucleic acid from the sample to hybridize to a complementary nucleic acid molecule (e.g., an oligonucleotide probe labeled using the compositions and methods of the present invention). A variety of hybridization assays using a variety of technologies for hybridization and detection are suitable for use in the detection of target nucleic acids. A description of a selection of assays is provided below.

a. Direct Detection of Hybridization

In some embodiments, hybridization of a nucleic acid sequence labeled using the compositions and methods of the present invention to the target sequence of interest is detected directly by visualizing a bound probe comprising a fluorescent or other label (e.g., a Northern or Southern assay; See e.g., Ausabel et al. (eds.), Current Protocols in Molecular Biology, John Wiley & Sons, NY [1991]). In these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A nucleic acid sequence labeled using the compositions and methods of the present invention specific for the target nucleic acid sequence being detected is allowed to contact the membrane under conditions of low, medium, or high stringency. Unbound labeled nucleic acid is removed and the presence of binding is detected by visualizing the labeled nucleic acid.

b. Detection of Hybridization Using "DNA Chip" Assays

In some embodiments of the present invention, target sequences are detected using a DNA chip hybridization assay. In this assay, a series of nucleic acid probes are affixed to a solid support. Each of the probes is designed to be unique to a given target sequence. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

In some embodiments, the nucleic acid to be analyzed is isolated, amplified by PCR, and labeled using the compositions and methods of the present invention. The labeled DNA is then incubated with the array using a fluidics station. The array is then inserted into a scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (nucleic acid sequences labeled using the compositions and methods of the present invention) (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or non-specifically bound DNA back into solution away from the capture probes. In some embodiments, a laser-based fluorescence scanner is then used to detect binding.

In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and removing by spinning.

DNA probes unique for the target sequence of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given target sequence. Batches of beads are combined to form a pool specific to the array. To perform an assay, the BEAD ARRAY is contacted with a prepared subject sample (e.g., DNA). Hybridization is detected using any suitable method.

C. Enzymatic Detection of Hybridization

In some embodiments, hybridization is detected by enzymatic cleavage of specific structures (e.g., the INVADER assay, Third Wave Technologies; See e.g., U.S. Pat. Nos. 5,846,717, 5,985,557, 5,994,069, 6,001,567, 6,090,543, 6,348,314, and 6,458,535, WO 97/27214 WO 98/42873, Lyamichev et al., Nat. Biotech., 17:292 (1999), Hall et al., PNAS, USA, 97:8272 (2000); each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. In some embodiments, the secondary probe oligonucleotide is 5'-end labeled using the compositions and methods of the present invention that is quenched by an internal dye. Upon cleavage, the de-quenched labeled product may be detected using a standard fluorescence plate reader.

The INVADER assay detects specific target sequences in unamplified genomic DNA. The isolated DNA sample is contacted with the first probe specific for the target sequence of interest and allowed to hybridize. Then a secondary probe, specific to the first probe, and containing the fluorescent or other label, is hybridized and the enzyme is added. Binding is detected by using a fluorescent plate reader and comparing the signal of the test sample to known positive and negative controls.

In other embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLI-TAQ GOLD DNA polymerase. A probe, specific for a given target sequence, is included in the PCR reaction. The probe consists of an oligonucleotide with a 5'-reporter dye (e.g., labeled using the compositions and methods of the present invention) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, target sequences are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label (e.g., using the compositions and methods of the present invention) to the nucleotide suspected of being at the target nucleic acid location. Incorporation of the label into the DNA can be detected by any suitable method (e.g., with a fluorimeter).

d. Other Detection Assays

The compositions and methods of the present invention find use in generating labeled nucleic acids for use in additional detection assays including, but not limited to, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884 and 6,183,960, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Bamay Proc. Natl. Acad. Sci USA 88, 189-93 (1991)); and sandwich hybridization methods (e.g., U.S. Pat. No. 5,288,609, herein incorporated by reference in its entirety).

In addition, the technologies available from a variety of commercial sources, including, but not limited to, Aclara BioSciences, Haywood, Calif.; Agilent Technologies, Inc., Palo Alto, Calif.; Aviva Biosciences Corp., San Diego, Calif.; Caliper Technologies Corp., Palo Alto, Calif.; Celera, Rockville, Md.; CuraGen Corp., New Haven, Conn.; Hyseq Inc., Sunnyvale, Calif.; Incyte Genomics, Palo Alto, Calif.; Applera Corp., Foster City, Calif.; Rosetta Inpharmatics, Kirkland, Wash.; and Sequenom, San Diego, Calif. are amenable to use with nucleic acid comprising labels incorporated using the compositions and methods of the present invention.

3. In Vivo and In Situ Applications

In some embodiments, the present invention provides in vivo and in situ methods that utilizing labeled nucleic acids. Such methods find use in the analysis of nucleic acids in cells and populations of cells in culture.

A. FACS

In some embodiments, labels are attached to nucleic acids (e.g., using the compositions and methods of the present invention) that bind to cell surfaces. A computer collects the fluorescence signature of each cell and displays the pattern of fluorescence for the user to analyze. In other applications, where one might want to separate cells which have a certain staining pattern from all other cells (e.g., due to binding to a labeled pre-selected antigen), the flow cytometry machine can direct those desired cells into a tube provided by the user. This is called fluorescence activated cell sorting (FACS).

B. FISH

In some embodiments, nucleic acids labeled using the compositions and methods of the present invention are used in FISH (Fluorescence In-Situ Hybridization) procedures. A FISH sample is prepared by using multiple probes, each of which binds to a different DNA sequence in the chromosomes in the sample. Each probe is labeled with a different dye (e.g., with different colors of emission spectra) or combination of two or more dyes.

Experimental

A. Methods

HPLC analyses were performed with a Hitachi D-7000 Interface, L-7100 gradient pump, and L-7400 UV detector using a Varian Omnisphere 5 C18 column (250×4.6 mm) and 100 mM TEAA, pH 7/Acetonitrile. MS analysis of all DNA-containing species was performed using a PerSeptive Biosystems Voyager-DE Biospectrometry Workstation V800520. MS analysis of small molecules was performed using an Applied Biosystems/MDS Sciex API365 LC/MS/MS triple quadrapole with an electrospray ionization source. Automated oligonucleotide synthesis was performed using a PerSeptive Biosystems Expedite Nucleic Acid Synthesis System. Silica gel was obtained from Aldrich (Milwaukee, Wis.). Analytical TLC was carried out on EM Science $F_{254}$ glass-backed fluorescence indicator plates. LCAA-CPG, used in the synthesis of 6, and 5'-Fluorescein phosphoramidite (FAM), used in the synthesis of 18, were both obtained from Glen Research (Sterling, Va.). Aleuritic acid was purchased from Lancaster Synthesis, Inc (Windham, N.H.). Hydroxyl-PEG-amine, MW 3400, was purchased from Shearwater Corporation (Huntsville, Ala.). DNA synthesis reagents and columns were purchased from Applied Biosystems (Foster City, Calif.). All other reagents were purchased from Aldrich and used without further purification. Solvents were dried over activated 3 Å molecular sieves. Nap-10 columns were purchased from Amersham Pharmacia Biotech (Uppsala, Sweden).

Synthesis of 2: A 250 ml round-bottom flask was charged with aleuritic acid 1 (2.2 g, 7.2 mmol) and 100 ml pyridine. 4,4'-dimethoxytrityl chloride was added slowly as a solid (3.2 g, 9.4 mmol). After 1 h, the reaction was concentrated by rotary evaporation and the reaction product was purified by column chromatography (70×230 mesh, 60A silica, 5% methanol/5% triethylamine/methylene chloride). The product was an off-white solid with a yield of 4.0 g, 90%. $R_f$=0.35 (10% methanol/5% triethylamine/methylene chloride). ESI-MS: calcd for $C_{37}H_{50}O_7$ $(M+K)^+$ 646, found 646.

Synthesis of 3: 2 (4.0 g, 6.6 mmol), N,N-diisopropylethylamine (8.5 g, 66 mmol), N-methylimidazole (1.6 g, 20 mmol), 60 ml tetrahydrofuran and 60 ml pyridine were combined in a 250 ml round-bottom flask. With stirring at 0° C. under argon flow, acetic anhydride (3.4 g, 33 mmol) was added via syringe. After 1 hour, the reaction mixture was concentrated by rotary evaporation. The crude reaction material was dissolved in methylene chloride (100 ml) and washed with saturated sodium chloride (100 ml). The crude reaction product was purified by column chromatography (70×230 mesh, 60A silica, 5% methanol/5% triethylamine/ mehtylene chloride). Compound 3 was obtained as a yellow oil (3.7 g, 81%). $R_f$=0.5 (5% methanol/5% triethylamine/ methylene chloride). ESI-MS: calcd for $C_{41}H_{54}O_9$0 $(M+K)^+$ 730, found 730.

Synthesis of 3a: 3 (see above, 1.6 g, 2.3 mmol) was dissolved in 100 ml tetrahydrofuran. N-hydroxysuccinimide (0.30 g, 2.6 mmol) and 1,3-dicyclohexylcarbodiimide (0.72 g, 3.5 mmol) were added as solids. The reaction mixture was stirred at room temperature for 16 hours under a drying tube and concentrated by rotary evaporation. Crude material 3a was purified by column chromatography (70×230 mesh, 60A silica, 50% ethyl acetate/50% hexane). The product was a white solid with a yield of 1.1 g, 60%. $R_f$=0.62 (75% ethyl acetate/25% hexane). ESI-MS: calcd for $C_{45}H_{57}NO_{11}$ (M+K)+827, found 827.

Synthesis of 4: A 100 ml round-bottom flask was charged with compound 3 (0.92 g, 1.3 mmol), 4-(dimethylamino) pyridine (210 mg, 1.7 mmol), 1,6-hexanediol (1.6 g, 13 mmol), and 50 ml tetrahydrofuran. 1,3-dicyclohexylcarbodiimide (3.0 g, 14.3 mmol) was added as a solid and the reaction mixture was stirred at room temperature under a drying tube for 16 hours. The reaction mixture was concentrated by rotary evaporation and the reaction product was purified by column chromatography (70×230 mesh, 60A silica, 2% triethylamine/49% ethyl acetate/49% hexane), yielded a white solid, 0.59 g, 59%. $R_f$=0.58 (75% ethyl acetate/25% hexane). ESI-MS: calcd for $C_{47}H_{66}O_{10}$ $(M+K)^+$ 830, found 830.

Synthesis of 5: 4 (0.59 g, 0.74 mmol), N,N-diisopropylethylamine (0.12 g, 0.89 mmol), and 4-(dimethylamino) pyridine (45 mg, 0.37 mmol) were combined in 50 ml tetrahydrofuran. Diglycolic anhydride (0.13 g, 1.1 mmol) was added as a solid, the reaction mixture was stirred for 3.5 h under a drying tube, and the solvent was then evaporated. The reaction product was purified by column chromatography (70×230 mesh, 60A silica, 5% methanol/5% triethylamine/methylene chloride). Compound 5 was obtained as pale yellow oil (0.44 g, 70%). $R_f$=0.31 (5% methanol/5% triethylamine/methylene chloride). ESI-MS: calcd for $C_{51}H_{70}O_{14}$ (M+H)+ 906, found 906.

Synthesis of 6: 4 g 1caa-CPG (Glen Research, #20-0001, 1000A, 69 μmol/g) was added to a 50 ml round-bottom flask. Compound 5 (0.36 g, 0.36 mmol) was dissolved in 20 ml pyridine and added to the CPG. 4-(dimethylamino)pyridine (24 mg, 0.20 mmol), triethylamine (0.16 g, 1.6 mmol), N-hydroxysuccinimide (91 mg, 0.79 mmol), and 1-ethyl-(3-dimethylaminopropyl)carbodiimide hydrochloride (0.30 g, 1.6 mmol) were added and the reaction mixture was vortexed at RT for 16 hours. Additional aliquots of 1-ethyl-(3-dimethylaminopropyl)carbodiimide hydrochloride (total of 0.60 g, 3.2 mmol) and 5 (total of 0.10 g, 0.01 mmol) were added to the reaction slurry to achieve a final loading of 5 of at least 20 μmol/g CPG. The support was filtered, washed with acetonitrile, and dried with argon flow. The material was capped with an equal mixture of 6% 4-(dimethylamino) pyridine in acetonitrile and 2/3/5 (acetic anhydride/2,4,6-collidine/acetonitrile) (100 ml total volume) for 2 h. The support was filtered, washed with pyridine, methanol, and methylene chloride, and dried overnight under vacuum. The loading was calculated by combining a known mass of CPG and known volume of 3% dichloroacetic acid/methylene chloride and measuring the absorbance of the solution at 504 nm to determine the concentration of the released trityl cation. The amount of 5 conjugated to the CPG was calculated to be 22.8 μmol/g CPG.

Synthesis of 10a: A 100 ml round-bottom flask was charged with material 3a (0.52 g, 0.66 mmol), N,N-diisopropylethylamine (0.13 g, 0.99 mmol), 6-amino-1-hexanol (0.093 g, 0.80 mmol), and 50 ml acetonitrile. The reaction mixture was stirred for 45 min at RT under a drying tube and concentrated by rotary evaporation. The reaction product was purified by column chromatography (70×230 mesh, 60A, 5% methanol/5% triethylamine/methylene chloride), yielding a pale yellow oil, 0.44 g, 84%. $R_f$=0.47 (5% methanol/5% triethylamine/methylene chloride). ESI-MS: calcd for $C_{47}H_{67}NO_9$ (M+K)+829, found 829.

Synthesis of 11a: Material 10a: (0.40 g, 0.51 mmol) was co-evaporated three times with 20 ml of acetonitrile and dissolved in 4 ml methylene chloride. 2-Cyanoethyl-N,N,N',N'-tetraisopropyl phosphorodiamidite (0.19 g, 0.61 mmol) was added, followed by the addition of a solution of 1H-tetrazole in acetonitrile (28 mg, 0.40 mmol/2 ml) with vigorous swirling. The reaction mixture was vortexed at RT for 2 hours. Methylene chloride (25 ml) was added to the reaction to increase the volume and the crude solution was washed with 25 ml 5% sodium bicarbonate/0.5% triethylamine. The organic layer was dried over magnesium sulfate for 10 minutes, filtered, concentrated, and co-evaporated twice with (20 ml) acetonitrile. The residue was dissolved in acetonitrile (15 ml) and dried over several granules of calcium hydride. The product solution was aliquoted (five aliquots of 3 ml, 100 μmol) into amber Expedite bottles, concentrated by aspiration vacuum, then dried under vacuum overnight in a dessicator containing phosphorus pentoxide (0.49 g, 98%). $R_f$=0.48 (5% triethylamine/dioxane).

Synthesis of 10b: A 100 ml round-bottom flask was charged with material 3a (0.18 g, 0.22 mmol), N,N-diisopropylethylamine (0.04 g, 0.29 mmol), $PEG_{3400}$-amine (0.50 g, 0.15 mmol), and 50 ml acetonitrile. The reaction mixture was stirred for 45 min at RT under a drying tube and concentrated by rotary evaporation. The crude product was purified by column chromatography (70×230 mesh, 60A, 2% methanol/5% triethylamine/methylene chloride). Compound 10b was obtained as a white solid with a yield higher than the theoretical value due to the hygroscopic character of the material. $R_f$=0.29 (5% methanol/5% triethylamine/methylene chloride). ESI-MS: calcd for $C_{195}H_{363}NO_{85}$ (M+H)+ 4080, product displayed a PEG mass dispersion centered around 4100.

Synthesis of 11b: Material 10b: (0.40 g, 0.01 mmol) was co-evaporated three times with 20 ml of acetonitrile and dissolved in 4 ml of methylene chloride. 2-Cyanoethyl-N,N,N',N'-tetraisopropyl phosphorodiamidite (0.04 g, 0.12 mmol) was added, followed by the addition of a solution of 1H-tetrazole in acetonitrile (5 mg, 0.08 mmol/ml) with vigorous swirling. The reaction mixture was vortexed at RT for 2 hours. Methylene chloride (25 ml) was added to the reaction to increase the volume, and the crude solution was washed with 25 ml of 5% sodium bicarbonate/0.5% triethylamine. The organic layer was dried over magnesium sulfate for 10 minutes, filtered, concentrated, and co-evaporated twice with 20 ml acetonitrile. The residue was dissolved in acetonitrile (3 ml) and dried over several granules of calcium hydride. The product solution was transferred in an amber Expedite bottle, concentrated by aspiration vacuum, then dried under vacuum overnight in a dessicator containing phosphorus pentoxide (0.23 g, 56%). $R_f$=0.69 (5% triethylamine/dioxane).

Synthesis of Mono-Dimethoxytrityl 1,12-Dodecanediol: Combined 1,12-dodecanediol (4 g, 20 mmol), N,N-diisopropylethylamine (1.3 g, 9.9 mmol) and 100 ml THF. 4,4'-dimethoxytrityl chloride (2.2 g, 6.6 mmol) was added slowly as a solid. After 1 h, the reaction was concentrated by rotary evaporation and the product was purified by column chromatography (70×230 mesh, 60A silica, 25% ethyl acetate/75% hexane), yielding a colorless oil, 3.3 g, 99%. $R_f$=0.39 (50% ethyl acetate/50% hexane). ESI-MS: calcd for $C_{33}H_{44}O_4$ (M+K)+543, found 543.

Synthesis of Dodecanediol Phosphoramidite: Mono-dimethoxytrityl 1,12-dodecanediol (0.60 g, 1.2 mmol) was co-evaporated three times with 20 ml acetonitrile and dissolved in 5 ml of methylene chloride. 2-Cyanoethyl-N,N,N',N'-tetraisopropyl phosphorodiamidite (0.43 g, 1.4 mmol) was added, followed by the addition of a solution of 1H-tetrazole in acetonitrile (64 mg, 0.92 mmol/3 ml) with vigorous swirling. The reaction mixture was vortexed at RT for 2 h. Methylene chloride (25 ml) was added to the reaction to increase the volume and the crude solution was washed with 25 ml of 5% sodium bicarbonate/0.5% triethylamine. The organic layer was dried over magnesium sulfate, filtered, concentrated, and coevaporated twice with acetonitrile. The residue was dissolved in acetonitrile (18 ml) and dried over several granules of calcium hydride. The product solution was aliquoted (6 aliquots of 3 ml, 200 μmol) into amber Expedite bottles, concentrated by aspiration vacuum, then dried under vacuum overnight in a dessicator containing phosphorus pentoxide (0.80 g, 96%). $R_f$=0.42 (75% ethyl acetate/25% hexane).

Cleavage and Deprotection of Aleuritic Acid Conjugated Oligonucleotides Leading to the Formation of 7, 12a, and 12b: After synthesis of the aleuritic acid DNA conjugate on a 1 µmol scale, the CPG support was transferred to a 4 ml sample vial with a Teflon-lined lid. A solution of 20% 0.4 M sodium hydroxide/methanol (1 ml) was added and the slurry was incubated for 3 h at 55° C. The solid material was separated by filtering through a 0.2 µm Teflon Acrodisc. The filtrate was neutralized with 4 µl of 80% acetic acid, dried, and desalted on a Nap-10 column.

Oxidation of Aleuritic Acid Conjugated Oligonucleotides (7, 12a and 12b) Leading to the Preparation of Aldehyde-Modified Probes (8, 13a and 13b): A 1 µmol synthesis of aleuritic acid DNA conjugate was dissolved in 0.9 ml of 100 mM sodium phosphate buffer, pH 7.6 and 0.1 ml of 100 mM sodium periodate in 100 mM sodium phosphate buffer, pH 7.6. The reaction vial was wrapped in foil, incubated for 30 min at RT, and purified on a Nap-10 column.

Coupling of Aldehyde-Modified Oligonucleotides to Amine-Containing Compounds, Preparation of 9a, 9b, and 15: A solution of amine (25 mmol) was prepared in 1 ml reaction buffer. The reaction buffer varied depending on the nature of the amine: (For synthesis of 9a, 25 mM sodium borate, pH 9.5; for the synthesis of 9b: 8% DMSO/25% methanol/25 mM sodium borate buffer, pH 9.5; for the synthesis of 15: 10% methanol/30% acetonitrile/25 mM sodium borate buffer, pH 9.5). The aldehyde labeled oligonucleotide (1 µmol) was dissolved in the appropriate amine-containing reaction buffer and 10 µL of 5 M sodium cyanoborohydride in 1 N sodium hydroxide was added. The pH of the reaction solution was adjusted to between 9 and 10 with either 80% acetic acid or 1 N sodium hydroxide and the reaction solution was incubated at RT. The crude reactions were monitored by HPLC analysis and, upon completion (3 hours), were purified on Nap-10 columns. The products (9a, 9b, and 13a) were analyzed by MS to confirm product formation.

Protocol for the Preparation of the 5'-aldehyde modified DNA Probes using C18 Oligonucleotide Purification Cartridge: The purification was performed using Supelco Supeldlean Envi-18, 1 g, 12 ml tubes. All additions were allowed to completely enter the gel bed before initiating the next step. The resin was equilibrated with one wash each of 5 ml methanol, 5 ml water, and 5 ml 0.5 M sodium chloride. The DNA sample was loaded onto the column in an equal volume of water and 0.5 M sodium chloride (3 ml total volume). The column was washed with 5 ml of 0.5 M sodium chloride, followed by a 1 ml addition of 100 mM sodium periodate solution which was allowed to incubate on the column for 15 minutes. The column was washed with 5 ml water, then with 1.5 ml of 10% methanol/water to elute the cleaved fragments. The final product was eluted with 1.5 ml of methanol/water 1:1.

B. Results

Attachment of Aleuritic Acid moiety to the 3'-loci of the DNA probes.

Figure 2:
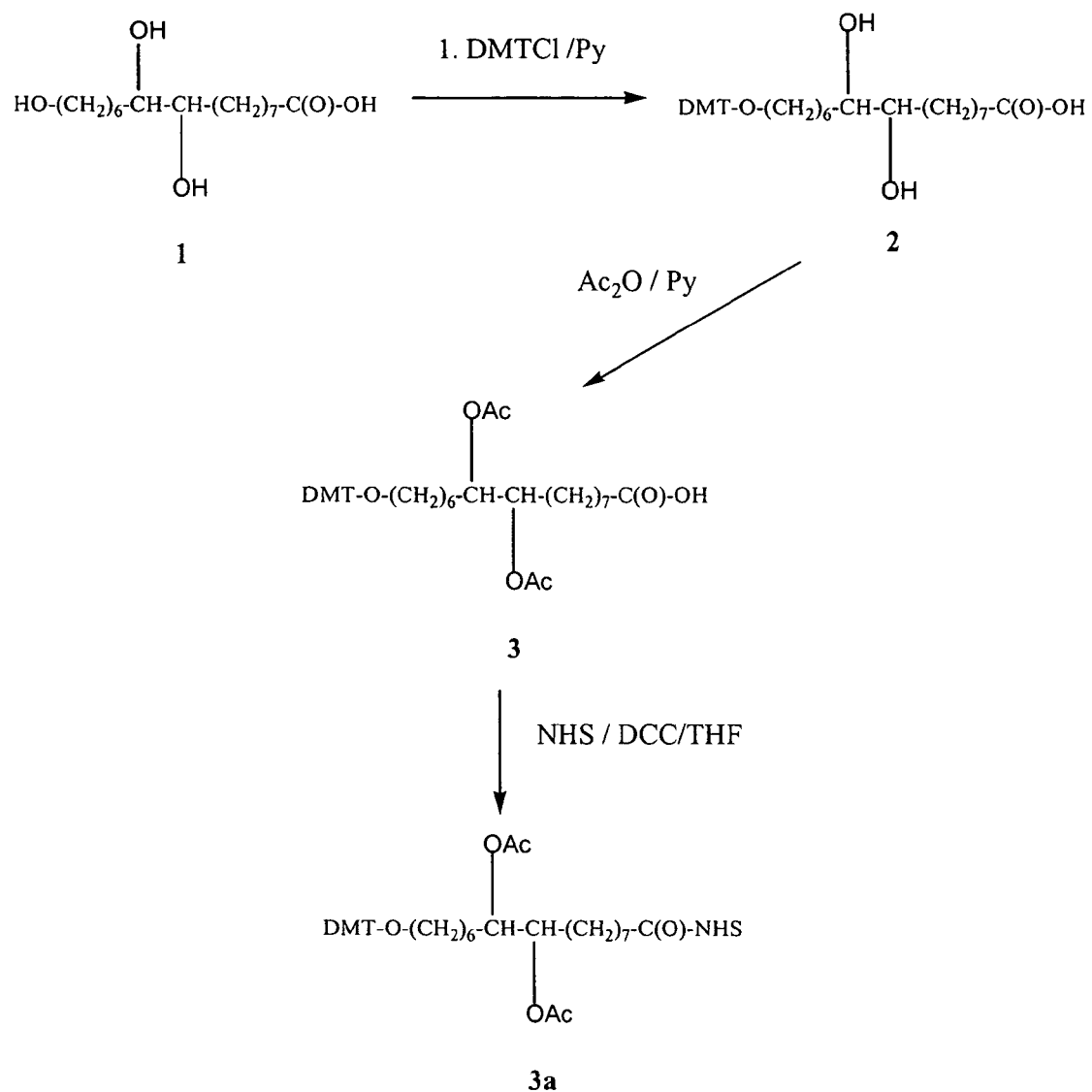

In the first step of the synthetic strategy, selectively protected derivatives of aleuritic acid 3 and 3a, which can serve as intermediates for further preparations of modified solid supports or for the synthesis of new phosphoramidite reagents, were prepared (FIG. 2). Known differences in the reactivity between the primary and secondary hydroxyl groups (Greene and Wuts, (1999) Protective Groups in Organic Synthesis; Chapter 2. John Wiley & Sons, Inc.) facilitated the synthesis and chromatographic isolation of the aleuritic acid derivative 2 with a DMT protected primary hydroxyl group. In the subsequent step of the procedure, derivative 2 was treated with acetic anhydride in pyridine and converted into intermediate compound 3, in which both the primary and the secondary hydroxyl groups were selectively protected with the DMT and the acetyl groups.

In the next step, the fully protected compound 3 was converted into the N-Hydroxysuccinimide (NHS) ester 3a. Synthesized ester 3a can serve as a key intermediate for the synthesis of a variety of reagents used in the introduction of the modification into DNA probes.

Figure 3:
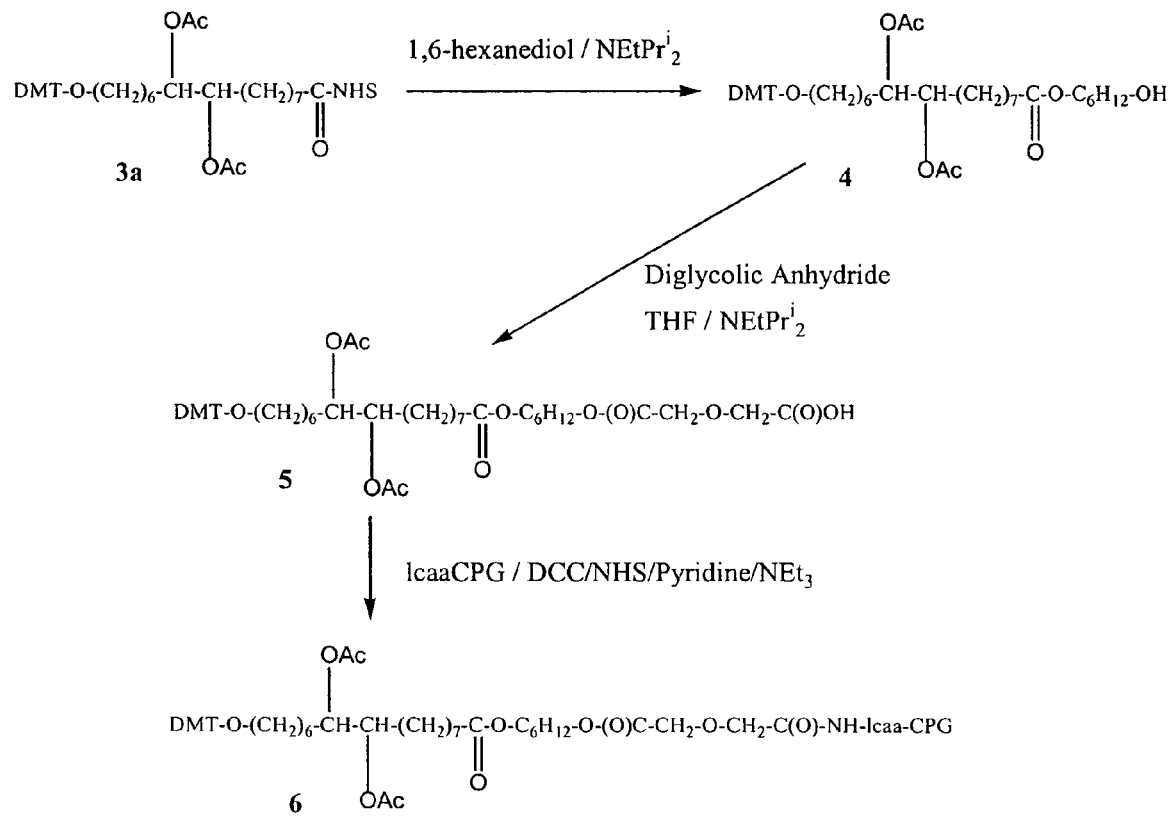
FIG. 3 shows steps in the preparation of the aleuritic acid CPG 6.

FIG. 3 illustrates the use of the active ester 3a in the preparation of a new CPG material modified with the aleuritic acid moiety. In the initial step, compound 3a was converted into the 1,6-hexanediol monoester 4. In the next step, the free hydroxyl group of the ester 4 was reacted with diglycolic anhydride (Pon and Yu, Nucleic Acid Res. 25:3629 [1997]) to form the diglycolic monoester 5. Finally, the diglycolic monoester 5 was coupled to the lcaa-CPG support, yielding solid support 6 modified with the aleuritic acid moiety. In all synthetic steps leading to the production of the solid support 6, standard reaction conditions and coupling protocols were employed (Letsinger and Lunsdorf (1976) J. Am. Chem. Soc. 98:3655-3661; Caruthers et al., (1987) Methods Enzymol. 154:287-313; Hovinen et al., (1993) Tetrahedron Lett. 34:5163-5166; Montserat et al., (1993) Nucleotides, Nucleosides 12:967-971; Guzaev et al., (1994) Tetrahedron 50:7203-7218; Pon and Yu (1997) Nucleic Acids Res. 25: 3629-3635). The efficiency of the coupling reaction of the diglycolic monoester 5 to the lcaa-CPG solid support was estimated by measuring the concentration of the DMT cation released from the support 6 after treatment with 3% dichloroacetic acid in dichloromethane. Typically, the observed loading of the DMT protected aleuritic acid on the synthesized solid support 6 was in the range of 22-26 µmol/g.

Figure 4:
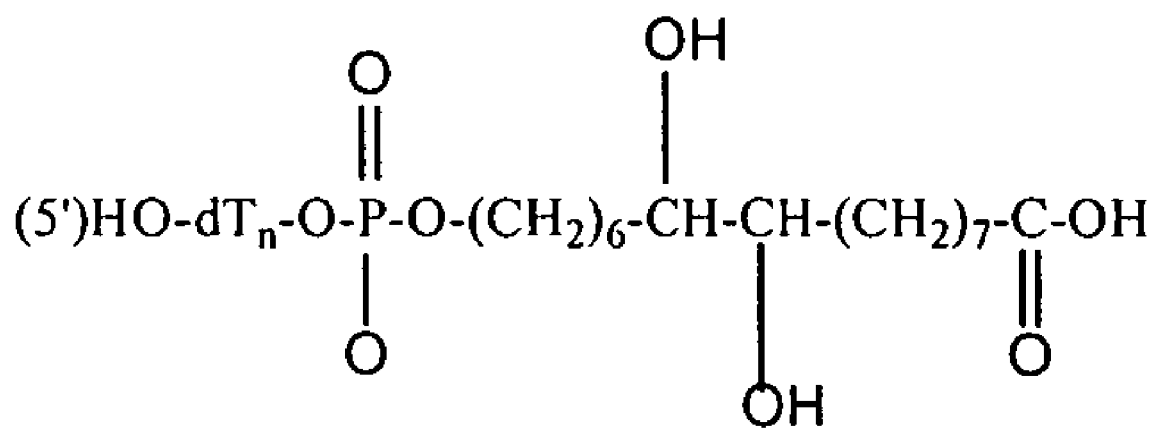
FIG. 4 shows the structure of the dT dinucleotide 7 (n=2), modified at its 3'-end with the aleuritic acid moiety.

To examine the applicability of the prepared solid support 6 to the synthesis of 3'-modified DNA probes, this material was tested under the conditions of automated oligonucleotide synthesis. To perform the synthesis, an appropriate amount of the solid support 6 containing 1 µmol of the attached aleuritic acid, was loaded into cartridges compatible with the PerSeptive Biosystems Expedite automated DNA synthesizer. The standard phosphoramidite coupling protocol was applied for the synthesis of the DNA probes. In the first experiment, a 3'-modified dinucleotide 7 (n=2) was synthesized as model material for the study of cleavage and deprotection conditions that would lead to formation of a final product with a deprotected carboxyl group and fully deprotected vicinal hydroxyl groups (FIG. 4).

Figure 5:
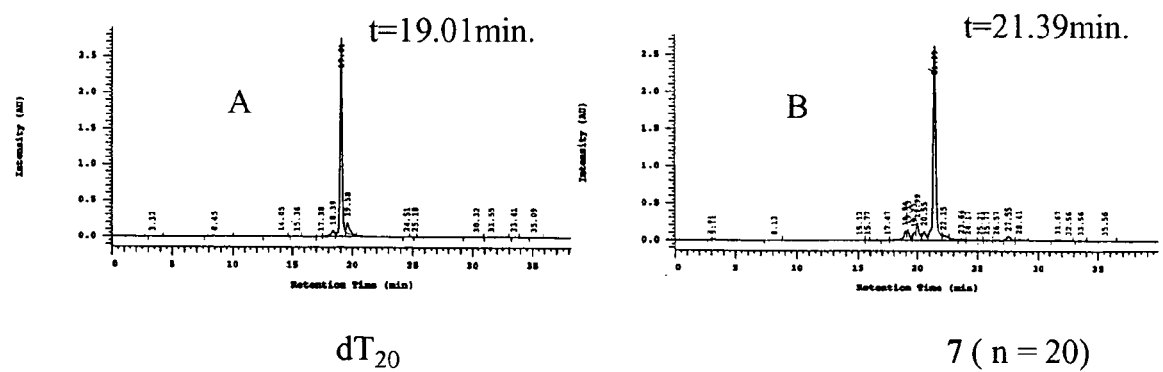
FIG. 5(A) shows RP HPLC of the crude unmodified $dT_{20}$ cleaved from the solid support with concentrated ammonia.
FIG. 5(B) shows RP HPLC of the 3'-modified probe 7 (n=20) cleaved from the solid support 6 with a solution of 80% methanol/20% 0.2M NaOH/$H_2O$ for 3 hours at 55° C.

In initial experiments with compound 7 (n=2), the standard protocol widely used for the cleavage and deprotection of chemically synthesized oligonucleotides (concentrated ammonia, 6 to 12 hours at 55° C.) was used (Letsinger and Lunsdorf, supra; Caruthers et al., supra; Beaucage and Iyer, supra; Protocols for Oligonucleotides and Analogs. Methods in Molecular Biology, Vol 20, Edited by Sudhir Agraval, Humana Press 1993). RP-HPLC analysis of the generated reaction product revealed that such deprotection conditions yielded multiple compounds regardless of the length of contact of the synthesized material with concentrated ammonia. The crude product of the cleavage and deprotection contained some compounds that were determined (by using extended incubation time of the crude reaction product in concentrated ammonia) to be incompletely deprotected final material. The nature of other compounds present in the crude material was not studied. Formation of a uniform and fully deprotected product 7 (n=2) was obtained by replacing the concentrated ammonia with a solution of 80% Methanol/ 20% 0.2M NaOH/H$_2$O and incubating the protected compound 7 (n=2) for 3 hours at 55° C. (Hovinen et al., (1993) Tetrahedron Lett. 34, 5163-5166). When this deprotection protocol was applied to the synthesis of longer, 3'-labeled oligonucleotides 7 (n=10 and n=20), the desired products were synthesized with efficiency and purity comparable to those achieved in the synthesis of unmodified dT oligomers of the same length. As an example, FIG. 5 compares the RP-HPLC analytical profile of crude material 7 (n=20), synthesized on solid support 6 and deprotected with a solution of 80% Methanol/20% 0.2M NaOH/H$_2$O for 3 hours at 55° C., to that of the crude 3'-unmodified dT-20-mer synthesized and deprotected according to the standard protocols.

Figure 6:
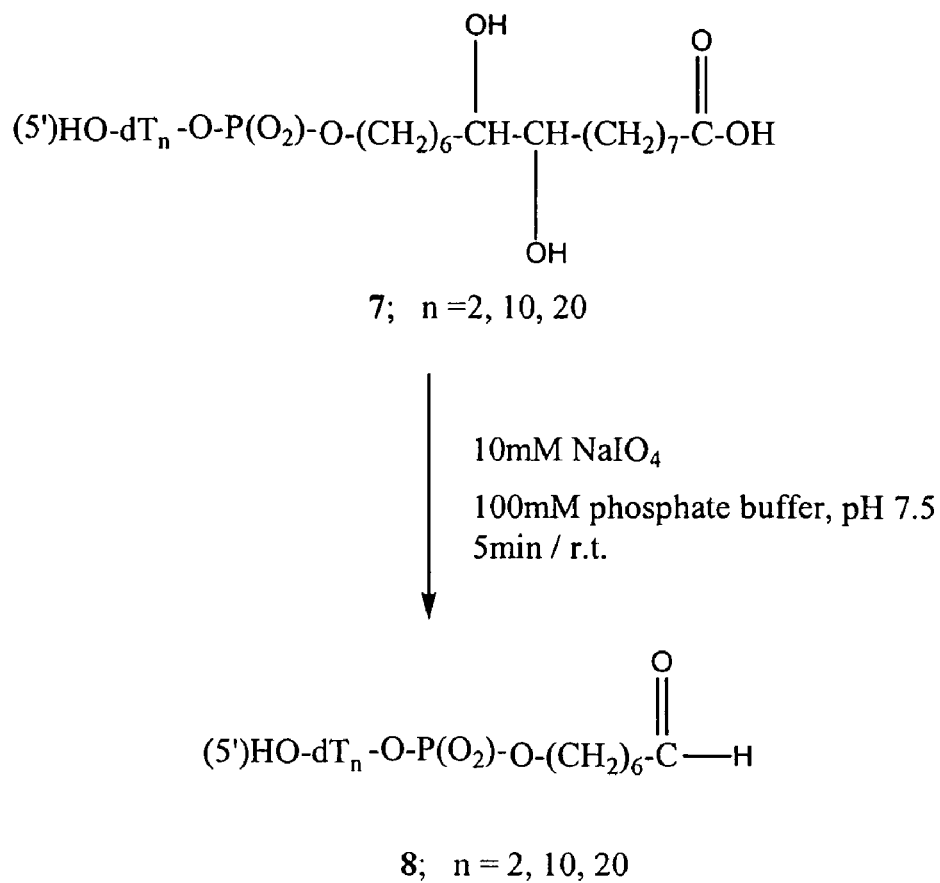
FIG. 6 shows sodium periodate oxidation of the aleuritic acid moiety attached to the 3'-loci of the probes 7 (n=2, 10, 20).

All synthesized compounds 7 (n=2,10, 20) labeled at their 3'-ends with the aleuritic acid moiety were isolated by RP HPLC, and their identities were confirmed by Mass Spectrometry. As mentioned above, the structural features of the aleuritic acid attached to the synthesized oligonucleotide probe allow for the efficient introduction of not only a carboxyl group but also a masked aldehyde group. Vicinal diols can be readily oxidized by a solution of sodium periodate under very mild conditions. This reaction leads to the bond cleavage between carbon atoms bearing vicinal hydroxyl groups and to the formation of two molecules containing aldehyde functional groups (Ermolinsky and Mikhailov (2000) Russian Journal of Bioorganic Chemistry 26, 429-449; Tilquin et al., (2001) Bioconjugate Chem.12, 451-457). The two newly formed molecules may be identical or different, depending on the symmetry of the oxidized vicinal diol. Such a synthetic approach was reported in a number of cases describing the preparation of aldehyde-modified DNA probes and the preparation of oligonucleotide bio-conjugates, as well as in the protocols of the immobilization of DNA probes onto solid surfaces (See e.g., Krotz et al., (2001) Bioorg. Med.Chem. Lett. 11:1863-1867; Greenberg and Kahl (2001) J. Org. Chem. 66:7151-7154; Czaplinski and Sheppard, (2001) J. Am. Chem. Soc. 123: 8618-8619). Previously synthesized compounds 7 (n=2,10 and 20) were selected as models to study the conditions of the sodium periodate oxidation of the vicinal hydroxyl groups present in the structure of aleuritic acid linked to the 3'-ends of the synthesized DNA probes 7 (FIG. 6).

Figure 7:
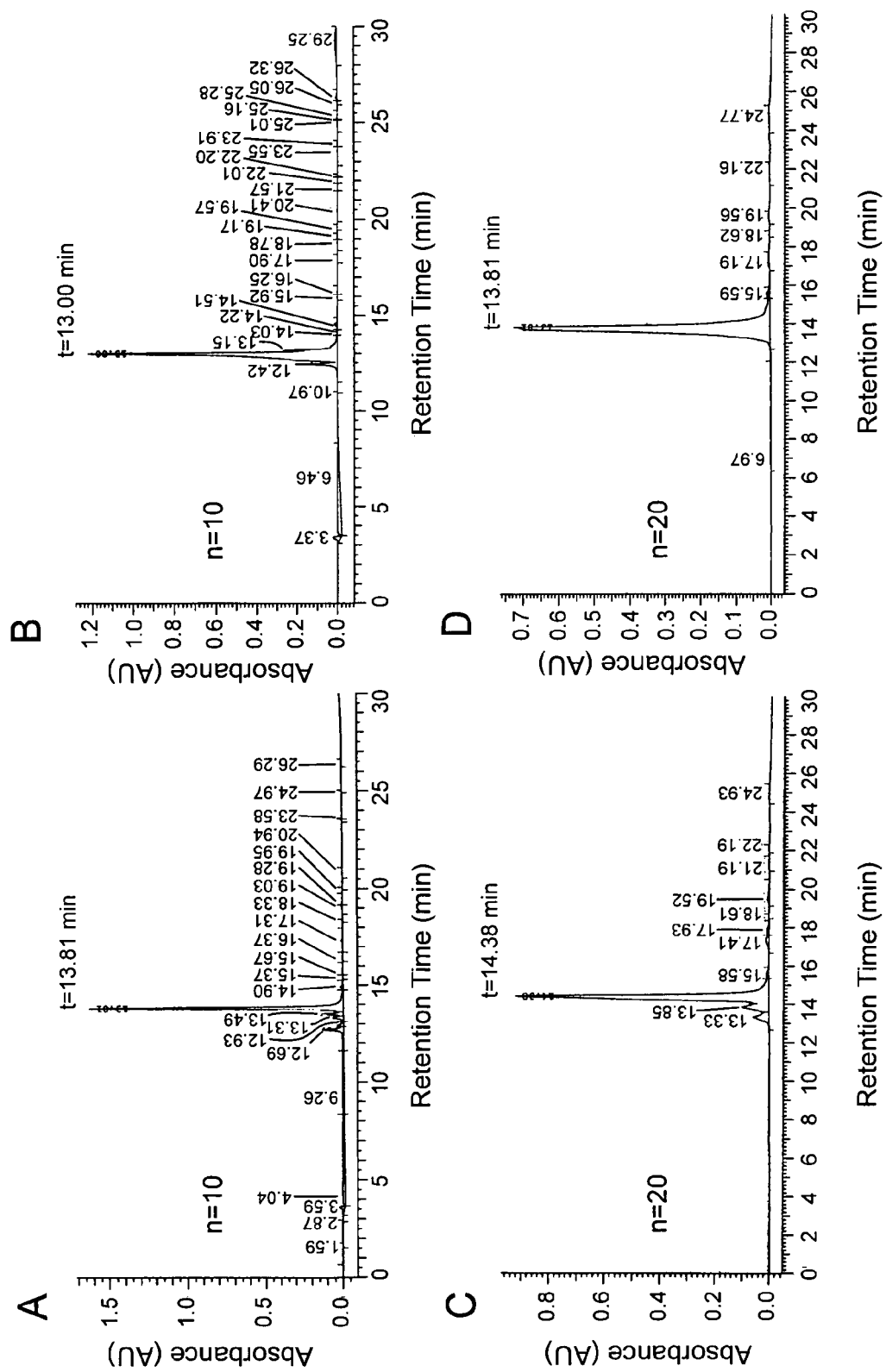
FIG. 7 shows RP HPLC analysis of the 3'-aleuritic acid labeled probes 7, (A) compound 7 (n=10); (C) compound 7 (n=20); and the RP HPLC analysis of the crude product of their oxidation with sodium periodate after 5 min (B) compound 8, (n=10); (D) compound 8, (n=20).

Oxidation of compounds 7 (n=2,10,20) was performed with 100 mM sodium periodate in 100 mM sodium phosphate buffer, pH 7.5, at room temperature (Urata et al., (1993) Tetrahedron Lett. 34,4015-4018; Hermanson, G.T. (1996) Bioconjugate techniques. Academic Press, pp.185-186). It was found that the corresponding 3'-aldehyde labeled DNA probes 8 (n=2, 10, 20) were formed quickly and efficiently. Monitoring the progress of the oxidation reaction by RP HPLC revealed that the full conversion of compounds 7 (n=10, 20) into the corresponding 3'-aldehyde labeled derivatives 8 (n=10, 20) occurred in less than 5 min (FIG. 7). The structure of the oxidation products 8 (n=2,10, 20), isolated by RP HPLC, were confirmed by Mass Spectrometry.

Figure 8:
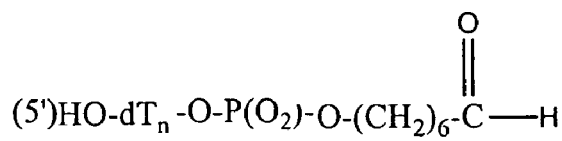
FIG. 8 shows a schematic of reductive amination coupling reaction of the 3'-aldehyde labeled probe 8(n=10) to 4,7,10,-trioxa-1,13-tridecanediamine and 1-pyrene methylamine.

To demonstrated the utility of synthesized 3'-aldehyde labeled probe 8, (n=10) as a starting material in the post-synthetic conjugation protocols, this material was used as a substrate in the reaction of the reductive amination with 1-pyrene methylamine and 4,7,10-trioxa-1,13-tridecanediamine (FIG. 8).

The conjugation of material 8 (n=10) to water soluble 4,7,10-trioxa-1,13-tridecanediamine proceeded with excellent yield under standard reaction conditions (Hermanson, G.T. (1996) Bioconjugate techniques. Academic Press, pp.185-186), producing conjugate 9a. The conjugation reaction of the 1-pyrene methylamine to material 8 (n=10), leading to the formation of the conjugate 9b, however, was negatively affected by the low solubility of the 1-pyrene methylamine hydrochloride in aqueous media. The use of a solvent system containing 25% Methanol and 8% of DMSO was necessary to achieve 60% coupling yield of the 1-pyrene methylamine to the 3'-aldehyde labeled probe 8 (n=10).

Phosphoramidites of Aleuritic Acid Derivatives.

Figure 10:
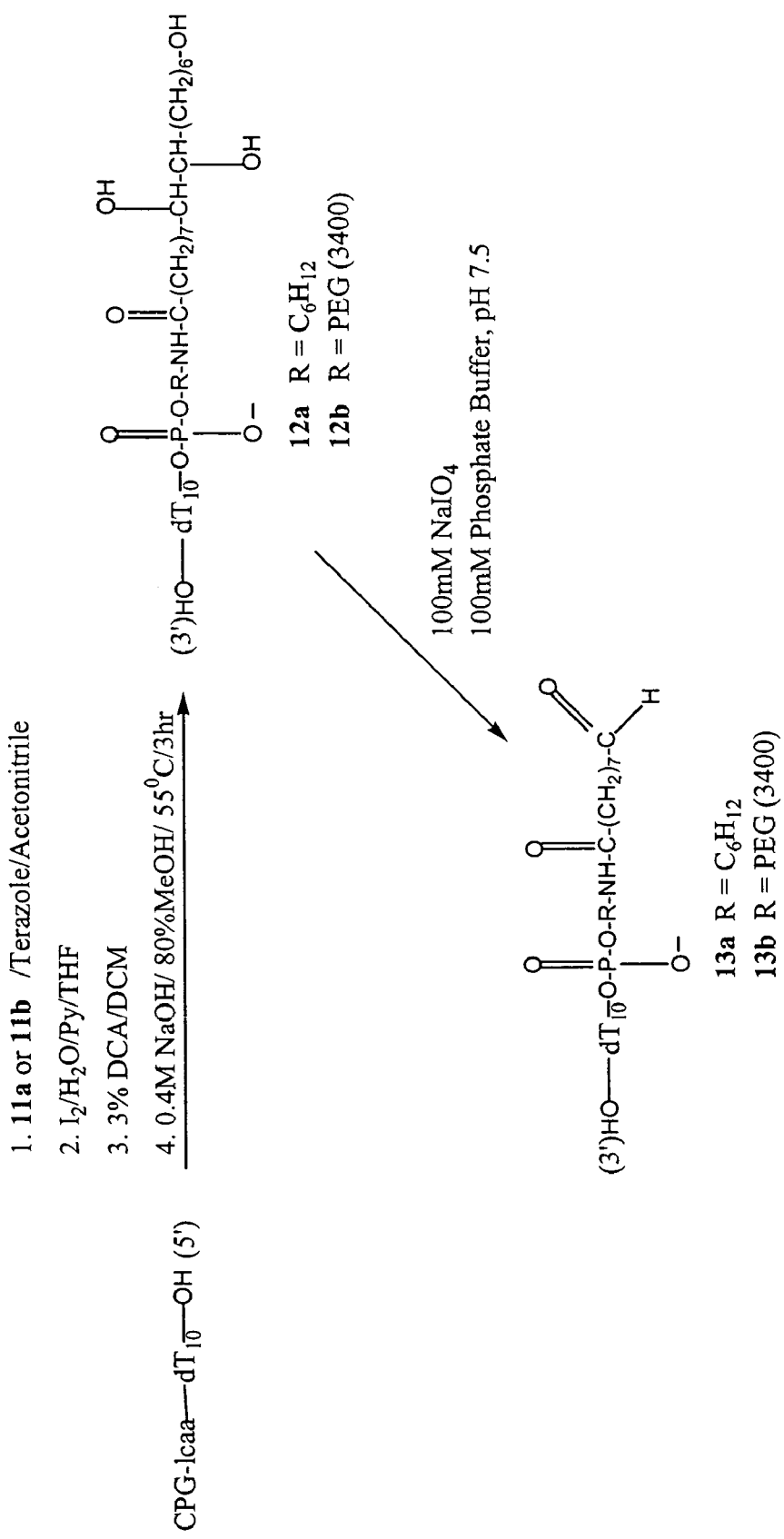
FIG. 10 shows a schematic of the synthesis of the 5'-aldehyde modified DNA probes 13a and 13b.

The synthetic approach is shown in FIG. 9. Group R in the synthesized phosphoramidites 11 can be selected from a variety of organic molecules, depending on the length of the linker or its desired chemical, physical or spectral properties (Shchepinov et al., (1997) Nucleic Acids Res. 25, 1155-1161; Watterson et al., (2000) Langmuir 16, 4984-4992; Steel et al., (2000) Biophys. J. 79, 975-81). As an example, two new phosphoramidites, phosphoramidite 11a, R═C$_6$H$_{12}$, and phosphoramidite 11b, R═PEG; M.W 3400 were synthesized. Both phosphoramidites Ha and 11b, were successfully applied as reagents in the automated synthesis of two different 5'-modified DNA probes 12a (n=2), R═C$_6$H$_{12}$ and 12b (n=10), R═PEG, M.W. 3400. Both DNA probes 12a and 12b were subsequently oxidized to the 5'-aldehyde modified probes 13a and 13b. (FIG. 10).

In the course of these experiments, phosphoramidites 11a and 11b were demonstrated to be fully compatible with the standard phosphoramidite protocol of automated DNA synthesis. In case of phosphoramidite 11b, however, a lower coupling yield was observed. Lower coupling efficiencies of phosphoramidite reagents used to introduce long linker molecules have been reported previously (Shchepinov et al., (1997) Nucleic Acids Res. 25, 1155-1161; Jäschke et al., (1993) Tetrahedron Lett. 34, 301-304). Due to their chemical and physiological properties, conjugates of Polyethylene glycol (PEG) with other biologically active molecules (enzymes, peptides, and oligonucleotides) represent a very important class of bio-conjugates (Greenwald et al., (2000) Crit. Rev. Ther. Drug Carrier Syst. 17, 101-61). Recent chemical literature reports many synthetic efforts leading to the preparation of such molecules (Bonora et al., (1997) Bioconjugate Chem. 8, 793-797; Jaschke et al., (1994) Nucleic Acids Res. 22, 4810-4817; Jaschke et al., (1996) Nucleosides, Nucleotides 15, 1519-1529; Jaschke et al., (1993) Tetrahedron Lett. 34, 301-304). This example demonstrates that the PEG modified oligonucleotide probe 12b, containing a masked aldehyde group, can be synthesized using phosphoramidite 11b in conjunction with the standard phosphoramidite protocol of automated oligonucleotide synthesis (FIG. 10). The effectiveness of the reductive amination reaction leading to the formation of the 3'-amino labeled compound 9a, led to a test of the efficiency of the reductive amination reaction between the 5'-aldehyde labeled compound 13a and bis-(3-aminopropyl)terminated polytetrahydroduran 14, (Average M$_n$ ca. 1,100) (FIG. 11).

It was found that the desired reaction product 15, in which the primary amino group was linked to the 5'-loci of the oligonucleotide thorough long, non-lipophilic polymeric linker, was formed with excellent yield. Analysis of the HPLC purified material 15 using Mass Spectrometry revealed the presence of the products, with mass equal to the sum of the masses of the compounds 13a and 14. Synthetic flexibility in the preparation of structurally different phosphoramidites 11 and the possibility of their combined use with phosphoramidites of other reagents opens new avenues allowing for the synthesis of structurally diverse DNA probes modified with the aldehyde group. Such probes can be used in the immobilization protocols of DNA probes onto solid surfaces (Afanassiev et al., (2000) Nucleic Acid Res. 28, E66-e66; Strother et al., (2001) Nucleic Acids Res. 29, 3535-3541; Podyminogin et al., (2001) Nucleic Acids Res.

29, 5090-5098; Lindroos et al., (2001) Nucleic Acids Res. 29, e69; Dombi et al., (2002) Synthesis 6, 816-824), and in the preparation of specific DNA conjugates, performance of which depends on the character and the length of the linker attached to the oligonucleotide moiety (Shchepinov et al., (1997) Nucleic Acids Res. 25, 1155-1161; Steel et al., (2000) Biophys. J. 79, 975-81).

Aleuritic Acid Phosphoramidites as Cleavable Linkers

Synthesized phosphoramidite 11a (R=$C_6H_{12}$) can be used not only as a reagent for the introduction of an aldehyde group into the 5'-end of the DNA probe, but also as a new type of cleavable linker (Horn et al., (1997) Nucleic Acids Res. 25, 4842-4849), useful in the preparation of specific DNA probes or conjugates.

The efficiency of this approach was tested by the synthesis of three model compounds 16-18, each containing two units that were linked by phosphoramidite 11a (R=$C_6H_{12}$) (FIG. 12).

The difference in size and chemical character between compounds 16-18 and the products of their sodium periodate oxidation, facilitated RP HPLC monitoring of the progress of cleaved product formation. At room temperature, the sodium periodate oxidation of the vicinal diols of the aleuritic acid linker in probes 16-18 was fast (less than 15 min) and led to the formation of the $dT_{10}$ DNA probes modified at their 5' or 3' ends with the aldehyde group.

Oligonucleotides modified with the aldehyde group and formed as products of the sodium periodate oxidation of compounds 16-18 were isolated by RP HPLC, and their identity was confirmed by Mass Spectrometry. The efficiency and ease with which the aleuritic acid linker was cleaved by the sodium periodate solution led to the development of a new, efficient method for the production of DNA probes labeled at the 5' end with the aldehyde group without time-consuming chromatographic purification of the final material. The method is conceptually similar to the "DMT-ON" purification protocol which is widely used in the separation of the "5'-DMT-ON", full length DNA sequences, from truncated fragments formed during the automated solid phase synthesis of oligonucleotides (McBride et al., (1988) Biotechniques 6, 362-7). The "DMT-ON" purification method uses commercially available C18-Oligonucleotide Purification Columns that are capable of retaining oligonucleotides modified with lipophilic (e.g., DMT) groups, while allowing elution of unmodified and truncated DNA fragments with an appropriate buffer. In the next step of the "DMT-ON" purification protocol, an acid solution is applied to the column, which leads to the cleavage of the DMT group from the retained full-length sequence. Subsequently, the full-length 5'-deprotected product is eluted from the column with another buffer addition. Generally, this purification protocol works well for 5'-DMT protected oligonucleotides. However, inherent instability of the DMT protecting group can occasionally cause its partial loss and, in consequence, the fill-length product may be eluted along with shorter fragments in the initial step of the purification.

In the method of the present invention, the "DMT ON" purification protocol was adapted, with a minor modification, to the preparation and purification of the 5'-aldehyde modified DNA probe synthesized with phosphoramidite 1a (R=$C_6H_{12}$). To ensure the presence of the lipophilic group at the 5'-loci of the synthesized material, phosphoramidite of the DMT protected 1-dodecanol was used to incorporate the desired, more stable (in comparison to the DMT group) moiety into the DNA probe 17. In the initial step of the developed method, crude product 17 (R=$C_{12}H_{25}$) was applied to the C18-OPC cartridge (Supelco, Supelclean Envi-18), and all truncated and unmodified oligonucleotide fragments were eluted according to the standard purification protocol. Next, 1 ml of the 100 mM solution of sodium periodate was applied on the column. After the solution sodium periodate was fully absorbed, the column was left for 15 min at room temperature. This step led to the oxidation and cleavage of the aleuritic acid of the 5'-modified DNA probe 17 still retained on the column and to the formation of the 5'-aldehyde modified DNA probe 13a. Subsequently, the sodium periodate solution was removed by washing the column with de-ionized water. Finally, the desired, 5'-aldehyde labeled, full-length product 13a was efficiently eluted using a methanol: water (1:1) solution. An HPLC analysis of the eluted material 13a demonstrated its high purity (FIG. 13). Mass Spectral analysis of the HPLC isolated material 13a confirmed its structure.

Figure 14:
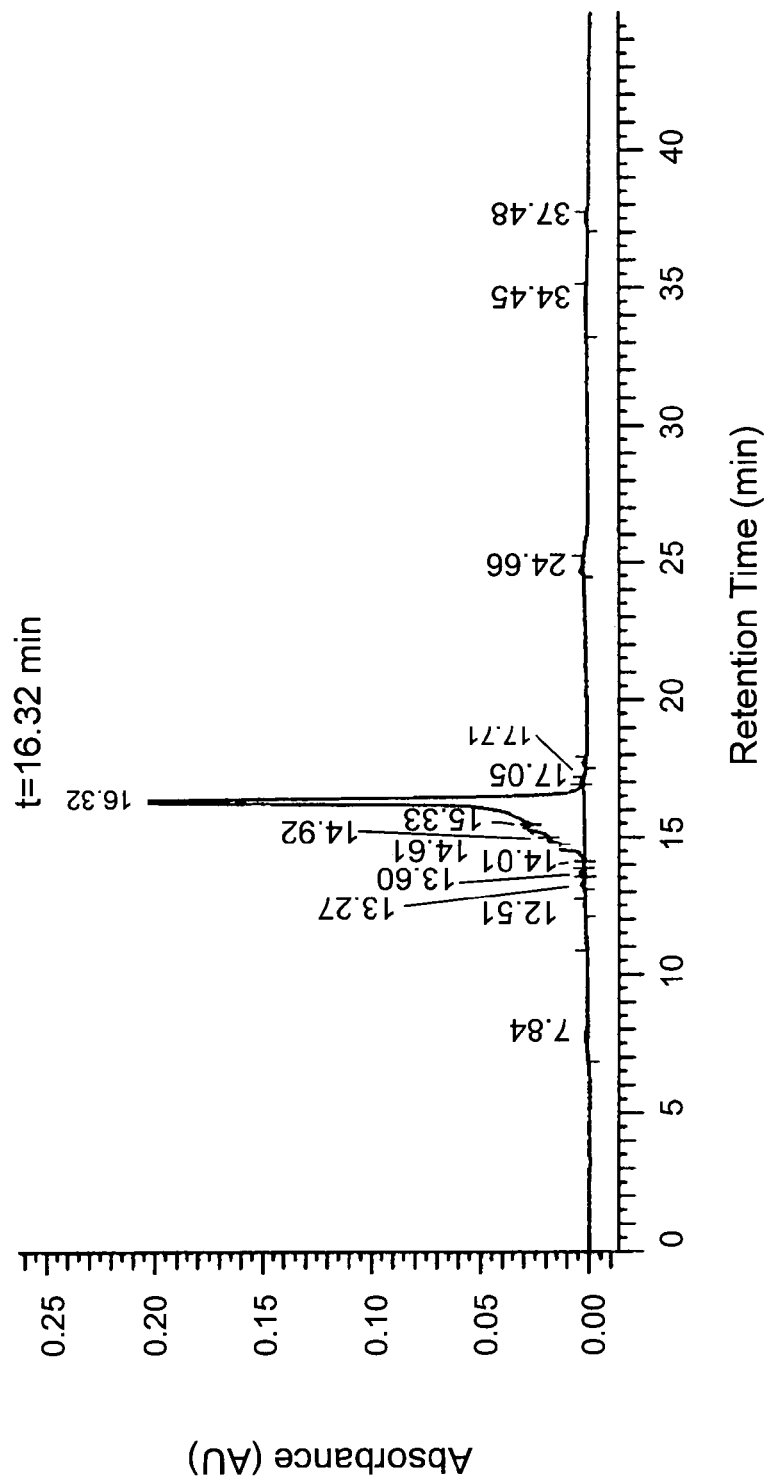
FIG. 14 shows the results of RP HPLC analysis of the material 13a eluted from the C18-OPC column.

FIG. 14 illustrates the RP HPLC analytical profile of the 5'-aldehyde modified probe 13a eluted from the C18-OPC cartridge. In conclusion, this example describes an efficient and versatile synthetic strategy that allows for the preparation of a broad range of new reagents.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A composition comprising:

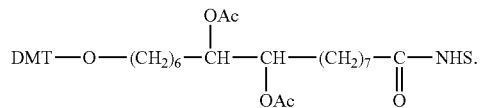

2. A controlled pore glass synthesis support comprising:

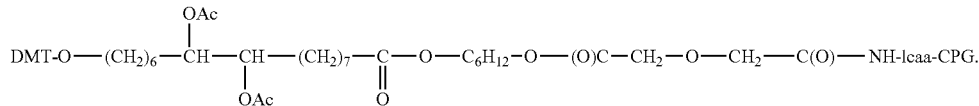

3. A phosphoramidite composition comprising:

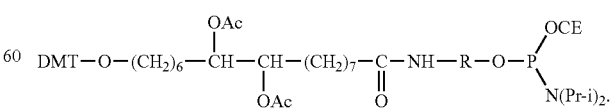

wherein R is selected from the group consisting of $C_6H_{12}$ and PEG(3400).

* * * * *